US011529148B2

(12) United States Patent
Meek et al.

(10) Patent No.: US 11,529,148 B2
(45) Date of Patent: Dec. 20, 2022

(54) INTRAMEDULLARY FIXATION SYSTEM FOR MANAGEMENT OF PELVIC AND ACETABULAR FRACTURES

(71) Applicants: The University of British Columbia, Vancouver (CA); British Columbia Cancer Agency Branch, Vancouver (CA)

(72) Inventors: Robert Meek, Vancouver (CA); Qingan Zhu, Vancouver (CA); Timothy Schwab, Vancouver (CA); Robin John Noel Coope, Vancouver (CA); Jared Slobodan, Vancouver (CA); Scott Young, Vancouver (CA)

(73) Assignees: The University of British Columbia, Vancouver (CA); British Columbia Cancer Agency Branch, Vancouver (CA)

( * ) Notice: Subject to any disclaimer, the term of this patent is extended or adjusted under 35 U.S.C. 154(b) by 0 days.

(21) Appl. No.: 15/952,093

(22) Filed: Apr. 12, 2018

(65) Prior Publication Data
US 2018/0296227 A1    Oct. 18, 2018

Related U.S. Application Data

(63) Continuation of application No. 14/300,752, filed on Jun. 10, 2014, now abandoned, which is a
(Continued)

(51) Int. Cl.
*A61B 17/16* (2006.01)
*A61B 17/72* (2006.01)

(52) U.S. Cl.
CPC ........ *A61B 17/164* (2013.01); *A61B 17/7208* (2013.01); *A61B 2017/1602* (2013.01)

(58) Field of Classification Search
CPC .............. A61B 17/164; A61B 17/7208; A61B 2017/1602
See application file for complete search history.

(56) References Cited

U.S. PATENT DOCUMENTS

| 2,328,270 A | 8/1943 | Daniel |
| 2,724,573 A | 11/1955 | Lundquist |
(Continued)

FOREIGN PATENT DOCUMENTS

| AT | 509852 A4 | 12/2011 |
| CN | 2662839 Y | 12/2004 |
(Continued)

OTHER PUBLICATIONS

European Patent Office, "Communication pursuant to Article 94(3) from EP Application No. 15850096.7", from Foreign Counterpart to U.S. Appl. No. 15/519,148, dated Oct. 15, 2019, pp. 1-5, Published: EP.
(Continued)

*Primary Examiner* — Kevin T Truong
*Assistant Examiner* — Tracy L Kamikawa
(74) *Attorney, Agent, or Firm* — Fortem IP LLP; Mary Fox

(57) ABSTRACT

Devices for treating a bone and methods of inserting such devices into a bone are disclosed. A device for treating a bone may include a flexible tube, a stiffening mechanism and an actuator. The flexible tube has a distal end and a proximal end. The stiffening mechanism within the flexible tube is configured to cause the flexible tube to become rigid. The actuator is configured to cause the stiffening mechanism to cause the flexible tube to become rigid in response to the actuator being actuated.

11 Claims, 14 Drawing Sheets

Related U.S. Application Data continuation of application No. 14/357,917, filed as application No. PCT/CA2012/050808 on Nov. 14, 2012, now Pat. No. 9,839,435.

(60) Provisional application No. 61/559,609, filed on Nov. 14, 2011.

(56) References Cited

U.S. PATENT DOCUMENTS

| | | | |
|---|---|---|---|
| 3,371,725 | A | 3/1968 | Wilhelm et al. |
| 4,098,351 | A | 7/1978 | Alessio |
| 4,489,792 | A | 12/1984 | Fahim et al. |
| 4,491,443 | A | 1/1985 | Decaro |
| 4,605,348 | A | 8/1986 | Decaro |
| 4,706,659 | A | 11/1987 | Matthews et al. |
| 5,108,397 | A | 4/1992 | White |
| 5,167,665 | A | 12/1992 | Mckinney |
| 5,234,435 | A | 8/1993 | Seagrave, Jr. |
| D346,218 | S | 4/1994 | White |
| 5,300,071 | A | 4/1994 | Browner et al. |
| 5,336,224 | A | 8/1994 | Selman |
| 5,527,309 | A | 6/1996 | Shelton |
| 5,527,310 | A | 6/1996 | Cole et al. |
| 5,593,407 | A | 1/1997 | Reis |
| 5,601,550 | A | 2/1997 | Esser |
| 5,649,925 | A | 7/1997 | Barbera Alacreu |
| 5,879,352 | A | 3/1999 | Filoso et al. |
| 5,944,719 | A | 8/1999 | Leban |
| 5,993,454 | A | 11/1999 | Longo |
| 6,209,886 | B1 | 4/2001 | Estes et al. |
| 6,340,362 | B1 | 1/2002 | Pierer et al. |
| 6,368,326 | B1 | 4/2002 | Dakin et al. |
| 7,258,692 | B2 | 8/2007 | Thelen et al. |
| 7,410,483 | B2 | 8/2008 | Danitz et al. |
| 7,625,395 | B2 | 12/2009 | Mückter |
| 7,632,277 | B2 | 12/2009 | Woll et al. |
| 7,785,325 | B1 | 8/2010 | Milbank |
| 7,846,162 | B2 | 12/2010 | Nelson et al. |
| 8,043,347 | B2 | 10/2011 | Jiang et al. |
| 8,128,626 | B2 | 3/2012 | Justin |
| 8,128,627 | B2 | 3/2012 | Justin et al. |
| 8,206,389 | B2 | 6/2012 | Huebner et al. |
| 8,372,074 | B2 | 2/2013 | Milbank |
| 8,409,257 | B2 | 4/2013 | Edidin et al. |
| 8,439,916 | B2 | 5/2013 | Coati et al. |
| 8,632,543 | B2 | 1/2014 | Metzinger et al. |
| 8,961,516 | B2 | 2/2015 | Nelson et al. |
| 9,060,809 | B2 | 6/2015 | Tipirneni et al. |
| 9,144,506 | B2 | 9/2015 | Phelps |
| 9,155,574 | B2 | 10/2015 | Saravia et al. |
| 9,482,260 | B1 | 11/2016 | Krause |
| 9,498,264 | B2 | 11/2016 | Harshman et al. |
| 9,532,789 | B2 | 1/2017 | Coope |
| 9,615,835 | B2 | 4/2017 | Lam et al. |
| 9,839,435 | B2 | 12/2017 | Meek et al. |
| 10,258,394 | B2 | 4/2019 | Harshman et al. |
| 10,307,188 | B2 | 6/2019 | Harshman et al. |
| 10,973,559 | B2 | 4/2021 | Harshman et al. |
| 2002/0032444 | A1 | 3/2002 | Mische |
| 2002/0087161 | A1 | 7/2002 | Randall et al. |
| 2002/0198527 | A1 | 12/2002 | Muckter |
| 2003/0078582 | A1 | 4/2003 | Heggeness |
| 2003/0181982 | A1 | 9/2003 | Kuslich |
| 2003/0187449 | A1 | 10/2003 | McCleary et al. |
| 2003/0229351 | A1 | 12/2003 | Tidwell et al. |
| 2004/0011565 | A1 | 1/2004 | Lyon et al. |
| 2004/0024409 | A1 | 2/2004 | Sand et al. |
| 2004/0050568 | A1 | 3/2004 | Orozco |
| 2004/0102778 | A1 | 5/2004 | Huebner et al. |
| 2004/0215191 | A1 | 10/2004 | Kitchen |
| 2005/0055023 | A1 | 3/2005 | Sohngen et al. |
| 2005/0085819 | A1 | 4/2005 | Ellis et al. |
| 2005/0154390 | A1 | 7/2005 | Biedermann et al. |
| 2005/0165401 | A1 | 7/2005 | Pack |
| 2006/0074421 | A1 | 4/2006 | Bickley et al. |
| 2006/0264950 | A1 | 11/2006 | Nelson et al. |
| 2007/0083204 | A1 | 4/2007 | Sidebotham |
| 2007/0162132 | A1 | 7/2007 | Messerli |
| 2007/0208364 | A1* | 9/2007 | Smith .................. A61M 29/00 606/191 |
| 2007/0233111 | A1 | 10/2007 | Orbay et al. |
| 2008/0051786 | A1 | 2/2008 | Jensen |
| 2008/0058722 | A1 | 3/2008 | Von et al. |
| 2008/0077133 | A1 | 3/2008 | Schulze |
| 2008/0077154 | A1 | 3/2008 | Edwards et al. |
| 2008/0108989 | A1 | 5/2008 | Parsell et al. |
| 2008/0161805 | A1 | 7/2008 | Saravia et al. |
| 2008/0181740 | A1 | 7/2008 | Waitszies |
| 2008/0195145 | A1 | 8/2008 | Bonutti et al. |
| 2008/0234676 | A1 | 9/2008 | Schulze et al. |
| 2008/0249628 | A1 | 10/2008 | Altarac et al. |
| 2008/0269745 | A1 | 10/2008 | Justin |
| 2008/0287951 | A1 | 11/2008 | Stoneburner et al. |
| 2008/0294163 | A1 | 11/2008 | Chou et al. |
| 2008/0294164 | A1 | 11/2008 | Frank et al. |
| 2008/0319455 | A1* | 12/2008 | Harris .................. A61F 5/0089 606/139 |
| 2009/0024174 | A1 | 1/2009 | Stark |
| 2009/0048672 | A1 | 2/2009 | Essenmacher |
| 2009/0062797 | A1 | 3/2009 | Huebner et al. |
| 2009/0149710 | A1* | 6/2009 | Stefanchik ............ A61B 1/005 600/146 |
| 2009/0192512 | A1 | 7/2009 | Sommers |
| 2009/0216232 | A1 | 8/2009 | Buford et al. |
| 2009/0228008 | A1* | 9/2009 | Justin .................. A61B 17/7266 606/62 |
| 2009/0299343 | A1* | 12/2009 | Rogers .............. A61M 25/0053 606/1 |
| 2010/0023010 | A1* | 1/2010 | Nelson ............... A61B 17/1717 606/62 |
| 2010/0076503 | A1 | 3/2010 | Beyar et al. |
| 2010/0185290 | A1 | 7/2010 | Compton et al. |
| 2010/0217333 | A1 | 8/2010 | Mcshane et al. |
| 2010/0249832 | A1 | 9/2010 | Stopek et al. |
| 2010/0249838 | A1 | 9/2010 | Stopek et al. |
| 2010/0249854 | A1 | 9/2010 | Thomas et al. |
| 2010/0249944 | A1 | 9/2010 | Thomas et al. |
| 2010/0262239 | A1 | 10/2010 | Boyden et al. |
| 2010/0286692 | A1 | 11/2010 | Greenhalgh et al. |
| 2010/0298893 | A1 | 11/2010 | Stucki et al. |
| 2010/0318137 | A1 | 12/2010 | Stucki et al. |
| 2010/0331842 | A1 | 12/2010 | Milbank |
| 2011/0015684 | A1 | 1/2011 | Belcheva et al. |
| 2011/0028974 | A1 | 2/2011 | Chemello |
| 2011/0040282 | A1 | 2/2011 | Uihlein |
| 2011/0046746 | A1 | 2/2011 | Rabiner et al. |
| 2011/0087227 | A1 | 4/2011 | Mazur et al. |
| 2011/0098757 | A1 | 4/2011 | Schelling |
| 2011/0098816 | A1 | 4/2011 | Jacob et al. |
| 2011/0098817 | A1 | 4/2011 | Eckhardt et al. |
| 2011/0119815 | A1 | 5/2011 | Paulson et al. |
| 2011/0144643 | A1 | 6/2011 | Lorenz et al. |
| 2011/0144645 | A1 | 6/2011 | Saravia et al. |
| 2011/0144703 | A1* | 6/2011 | Krause ................ A61B 17/869 606/309 |
| 2011/0153454 | A1 | 6/2011 | Dunn et al. |
| 2011/0184518 | A1 | 7/2011 | Trieu |
| 2011/0184519 | A1 | 7/2011 | Trieu |
| 2011/0184520 | A1 | 7/2011 | Trieu |
| 2011/0196435 | A1 | 8/2011 | Forsell |
| 2011/0230966 | A1 | 9/2011 | Trieu |
| 2011/0238181 | A1 | 9/2011 | Trieu |
| 2011/0264229 | A1 | 10/2011 | Donner |
| 2011/0288598 | A1 | 11/2011 | Moed et al. |
| 2011/0306975 | A1 | 12/2011 | Kaikkonen et al. |
| 2011/0319944 | A1 | 12/2011 | Borodic |
| 2012/0010617 | A1 | 1/2012 | Ramos Maza |
| 2012/0065638 | A1 | 3/2012 | Moore |
| 2012/0078252 | A1 | 3/2012 | Huebner et al. |
| 2012/0078311 | A1 | 3/2012 | Huebner et al. |
| 2012/0083847 | A1 | 4/2012 | Huebner et al. |
| 2012/0083895 | A1 | 4/2012 | Conway et al. |
| 2012/0101533 | A1 | 4/2012 | Purcell et al. |

(56) References Cited

U.S. PATENT DOCUMENTS

| | | |
|---|---|---|
| 2012/0101576 A1 | 4/2012 | Dewey et al. |
| 2013/0006145 A1 | 1/2013 | Toomey et al. |
| 2013/0006245 A1 | 1/2013 | Stoneburner et al. |
| 2013/0012942 A1 | 1/2013 | Nelson et al. |
| 2013/0131678 A1 | 5/2013 | Dahners |
| 2013/0144348 A1 | 6/2013 | Schwappach |
| 2013/0325007 A1 | 12/2013 | Beyar et al. |
| 2014/0114312 A1 | 4/2014 | Krause |
| 2014/0309636 A1 | 10/2014 | Meek et al. |
| 2014/0358146 A1 | 12/2014 | Meek et al. |
| 2015/0038970 A1 | 2/2015 | Coope |
| 2015/0157370 A1 | 6/2015 | Gross |
| 2015/0257800 A1 | 9/2015 | Harshman et al. |
| 2015/0297245 A1 | 10/2015 | Lam et al. |
| 2017/0014170 A1 | 1/2017 | Fallin et al. |
| 2017/0020585 A1 | 1/2017 | Harshman et al. |
| 2017/0049460 A1 | 2/2017 | Coope |
| 2017/0164953 A1 | 6/2017 | Lam et al. |
| 2017/0238977 A1 | 8/2017 | Harshman et al. |
| 2018/0092681 A1 | 4/2018 | Lutz |
| 2019/0231401 A1 | 8/2019 | Harshman et al. |
| 2019/0282280 A1 | 9/2019 | Harshman et al. |
| 2020/0054372 A1 | 2/2020 | Stinson et al. |
| 2021/0220027 A1 | 7/2021 | Harshman et al. |
| 2021/0353338 A1 | 11/2021 | Meek et al. |
| 2021/0386465 A1 | 12/2021 | Thaler et al. |

FOREIGN PATENT DOCUMENTS

| | | |
|---|---|---|
| CN | 2699846 | 5/2005 |
| CN | 101208053 A | 6/2008 |
| CN | 101633119 A | 1/2010 |
| CN | 101636119 A | 1/2010 |
| CN | 102793579 A | 11/2012 |
| CN | 103813764 A | 5/2014 |
| CN | 104203132 A | 12/2014 |
| CN | 104203132 B | 8/2017 |
| CN | 107106217 A | 8/2017 |
| CN | 112955087 A | 6/2021 |
| EP | 0078619 A2 | 5/1983 |
| EP | 1941838 A1 | 7/2008 |
| EP | 2779928 A1 | 9/2014 |
| EP | 3326558 A1 | 5/2018 |
| EP | 3206608 | 7/2018 |
| EP | 3522803 A1 | 8/2019 |
| EP | 3866712 A1 | 8/2021 |
| GB | 1494553 A | 12/1977 |
| WO | 2007009123 A2 | 1/2007 |
| WO | 2008116175 A2 | 9/2008 |
| WO | 2008120877 A1 | 10/2008 |
| WO | 2009143374 A2 | 11/2009 |
| WO | 2010124230 A1 | 10/2010 |
| WO | 2011067668 A1 | 6/2011 |
| WO | 2011119815 A2 | 9/2011 |
| WO | 2011153454 A2 | 12/2011 |
| WO | 2012107913 A2 | 8/2012 |
| WO | 2013063145 A1 | 5/2013 |
| WO | 2013071432 A1 | 5/2013 |
| WO | 2014075165 A1 | 5/2014 |
| WO | 2014075184 A1 | 5/2014 |
| WO | 2015134750 A1 | 9/2015 |
| WO | 2016061173 A1 | 4/2016 |
| WO | 2018067888 A1 | 4/2018 |
| WO | 2020077457 A1 | 4/2020 |

OTHER PUBLICATIONS

Canadian Intellectual Property Office, "Notice of Allowance from CA Application No. 2964370", from Foreign Counterpart to U.S. Appl. No. 15/519,148, dated Dec. 13, 2019, p. 1, Published: CA.

Canadian Intellectual Property Office, "Office Action from CA Application No. 2978697 dated Oct. 19, 2018", from Foreign Counterpart to PCT Application No. PCT/US2015/018969, dated Oct. 19, 2018, pp. 1-4, Published: CA.

U.S. Patent and Trademark Office, "Notice of Allowance", U.S. Appl. No. 15/285,811, dated Mar. 25, 2019, pp. 1-11, Published: US.

International Bureau, "International Preliminary Report on Patentability from PCT Application No. PCT/US2017/055442 dated Apr. 18, 2019", from Foreign Counterpart to U.S. Appl. No. 16/340,067, pp. 1-8, Published: WO.

European Patent Office, "Communication pursuant to Article 94(3) from EP Application No. 17207050.0 dated Jul. 22, 2019", from Foreign Counterpart to U.S. Appl. No. 14/357,917, pp. 1-5, Published: EP.

U.S. Patent and Trademark Office, "Notice of Allowance", U.S. Appl. No. 15/519,148, dated Feb. 13, 2019, pp. 1-42, Published: US.

Canadian Intellectual Property Office, "Office Action from CA Application No. 2,964,370 dated Jan. 24, 2019", from Foreign Counterpart to U.S. Appl. No. 15/519,148, dated Jan. 24, 2019, pp. 1-6, Published: CA.

China National Intellectual Property Office, "Office Action from CN Application No. 201580061380.2 dated Dec. 21, 2018", from Foreign Counterpart to U.S. Appl. No. 15/519,148, dated Dec. 21, 2018, pp. 1-18, Published: CN.

Canadian Intellectual Property Office, "Office Action from CA Application No. 2855752 dated Jun. 17, 2019", from Foreign Counterpart to U.S. Appl. No. 14/357,917, pp. 1-3, Published: CA.

U.S. Patent and Trademark Office, "Office Action for U.S. Appl. No. 15/285,811 dated Oct. 18, 2018", pp. 1-39, Published in: US.

China National Intellectual Property Administration, "Notice of Decision of Granting Patent Right for Invention from CN Application No. 201580061380.2 dated Sep. 10, 2019", from Foreign Counterpart to U.S. Appl. No. 15/519,148, pp. 1-5, Published: CN.

"UT Southwest Medical Surgeons Market Pelvic Fracture Device," accessed at http://www.texasbusiness.com/ut-southwest-medical-surgeons-market-pelvic-fracture-device-cms-4418, Apr. 22, 2011, Texas Business.com, 5 Pages.

Barry, M., and Paterson, J. M. H., "Flexible intramedullary nails for fractures in children," The Journal of Bone & Joint Surgery Br., vol. 86-B, No. 7, pp. 947-953, © 2004 British Editorial Society of Bone and Joint Surgery (Sep. 2004).

Canada Intellectual Property Office, "Office Action for CA Application No. 2,855,752", "Foreign Counterpart to U.S. Appl. No. 14/357,917", dated Mar. 9, 2018, pp. 1-5, Published in: CA.

Canadian Intellectual Property Office, "Office Action for CA Application No. 2,855,752", "Foreign Counterpart to U.S. Appl. No. 14/357,917", dated Feb. 3, 2017, pp. 1-4, Published in: CA.

Canadian Intellectual Property Office, "Office Action for CA Application No. 2,855,752", "Foreign Counterpart to U.S. Appl. No. 14/357,917", dated Oct. 28, 2015, pp. 1-4, Published in: CA.

Cheung, et al., "A new halo-pelvic apparatus", Spine, (2003), vol. 28, No. 3, pp. 305-308.

European Patent Office, "Communication under Rule 71(3) for EP Application No. 12849005.9", Foreign Counterpart to U.S. Appl. No. 14/357,917, dated Jul. 25, 2017, pp. 1-6, Published in: EP.

European Patent Office, "Communication Pursuant to Article 94(3) for EP Application No. 12849005.9", Foreign Counterpart to U.S. Appl. No. 14/357,917, dated Jun. 2, 2016, pp. 1-4, Published in: EP.

Extended European Search Report for European Patent Application No. 12849005.9, dated Jun. 15, 2015 (6 pages).

Ganz, R., et al., "Surgical dislocation of the adult hip," The Journal of Bone & Joint Surgery Br., vol. 83-B, No. 8, pp. 1119-1124 (Nov. 2001).

Griffin, D.R., et al., "Vertically unstable pelvic fractures fixed with percutaneous iliosacral screws: does posterior injury pattern predict fixation failure?," Journal of Orthopaedic Trauma, vol. 20, No. 1 (Supplement), pp. S30-S36, Lippincott Williams & Wilkins (Jan. 2006).

International Search Report and Written Opinion for International Application No. PCT/US2015/018969 dated May 27, 2015, pp. 5.

International Search Report and Written Opinion for International Application No. PCT/US2015/055441 dated Feb. 9, 2016, pp. 12.

International Search Report for International Application No. PCT/CA2012/050808, dated Feb. 26, 2013. (5 pages).

(56) References Cited

OTHER PUBLICATIONS

IP Australia, "Patent Examination Report No. 1 for AU Application No. 2012339536", Foreign Counterpart to U.S. Appl. No. 14/357,917, dated Jan. 23, 2015, pp. 1-5, Published in: AU.
IP Australia, "Patent Examination Report No. 2 for AU Application No. 2012339536", Foreign Counterpart to U.S. Appl. No. 14/357,917, dated Oct. 16, 2015, pp. 1-6, Published in: AU.
Miller, A.N., and Routt, M.L.C.Jr., "Variations in Sacral Morphology and Implications for Iliosacral Screw Fixation," Journal of the American Academy of Orthopaedic Surgeons, vol. 20, No. 1, pp. 8-16 (Jan. 2012).
Non-Final Office Action in U.S. Appl. No. 14/300,752 dated Oct. 20, 2014 (15 pages).
Novick, N., "Pelvic Fractures/Acetabular Fractures—An Interview with Dr. David L. Helfet," Hospital for Special Surgery, accessed at http://www.hss.edu/conditions-pelvic-acetabulum-fractures.asp, Mar. 30, 2006, 10 pages.
Starr, A.J., and Malekzadeh, A.S., "Fractures of the Pelvic Ring," in Rockwood & Green's Fractures in Adults 6th Edition, Chapter—41, Lippincott Williams & Wilkins, pp. 40 (2006).
Starr, A.J., et al., "Superior pubic ramus fractures fixed with percutaneous screws: what predicts fixation failure?" Journal of Orthopedic Trauma, vol. 22, No. 2, pp. 81-87 (Feb. 2008).
State Intellectual Property Office of the People's Republic of China, "Search Report for CN Application No. 201280066180.2 dated Aug. 10, 2016", Foreign Counterpart to U.S. Appl. No. 14/357,917, dated Aug. 10, 2016, pp. 1-3.
State Intellectual Property Office, P.R. China, "First Office Action for CN Application No. 201280066180.2 dated Dec. 28, 2015", Foreign Counterpart to U.S. Appl. No. 14/357,917, dated Dec. 28, 2015, pp. 1-7, Published in: CN.
State Intellectual Property Office, P.R. China, "Second Office Action for CN Application No. 201280066180.2 dated Aug. 3, 2016", "Foreign Counterpart to U.S. Appl. No. 14/357,917", dated Aug. 3, 2016, pp. 1-6, Published in: CN.
State Intellectual Property Office, P.R. China, "Third Office Action for CN Application No. 201280066180.2 dated Jan. 5, 2017", Foreign Counterpart to U.S. Appl. No. 14/357,917, dated Jan. 5, 2017, pp. 1-4, Published in: CN.
U.S. Patent and Trademark Office, "Restriction Requirement for U.S. Appl. No. 14/357,917", dated Jan. 21, 2016, pp. 1-6, Published in: US.
U.S. Patent and Trademark Office, "Advisory Action for U.S. Appl. No. 14/300,752", dated Oct. 7, 2015, pp. 1-3, Published in: US.
U.S. Patent and Trademark Office, "Advisory Action for U.S. Appl. No. 14/300,752", dated Feb. 16, 2017, pp. 1-3, Published in: US.
U.S. Patent and Trademark Office, "Final Office Action for U.S. Appl. No. 14/300,752", dated Jan. 12, 2018, pp. 1-18, Published in: US.
U.S. Patent and Trademark Office, "Final Office Action for U.S. Appl. No. 14/300,752", dated Nov. 3, 2016, pp. 1-15, Published in: US.
U.S. Patent and Trademark Office, "Final Office Action for U.S. Appl. No. 14/300,752", dated May 28, 2015, pp. 1-14, Published in:US.
U.S. Patent and Trademark Office, "Final Office Action for U.S. Appl. No. 14/357,917", dated Sep. 6, 2016, pp. 1-11, Published in: US.
U.S. Patent and Trademark Office, "Notice of Allowance for U.S. Appl. No. 14/357,917", dated Jul. 26, 2017, pp. 1-5, Published in: US.
U.S. Patent and Trademark Office, "Office Action for U.S. Appl. No. 14/300,752", dated Aug. 8, 2017, pp. 1-16, Published in: US.
U.S. Patent and Trademark Office, Office Action for U.S. Appl. No. 14/300,752, dated Apr. 5, 2016, pp. 1-16, Published in: US.
U.S. Patent and Trademark Office, "Office Action for U.S. Appl. No. 14/357,917", dated Apr. 18, 2016, pp. 1-10, Published in: US.
U.S. Pat. No. 7,273,482, (withdrawn)

Vaidya, R., et al., "Complications of Anterior Subcutaneous Internal Fixation for Unstable Pelvis Fractures: A Multicenter Study," Clinical Orthopaedicsand Related Research, vol. 470, No. 8, pp. 2124-2131 (Aug. 2012).
Canadian Intellectual Property Office, "Office Action from CA Application No. 2,964,370 dated May 4, 2018", from Foreign Counterpart to PCT Application No. PCT/US2015/055441, dated May 4, 2018, pp. 1-7, Published: CA.
European Patent Office, "Communication pursuant to Article 94(3) from EP Application No. 12849005.9 dated Nov. 25, 2016", from Foreign Counterpart to PCT Application No. PCT/CA2012/050808, dated Nov. 25, 2016, pp. 1-4, Published: EP.
European Patent Office; "Extended European Search Report from EP Application No. 15850096.7 dated Jun. 8, 2018"; from Foreign Counterpart of U.S. Appl. No. 15/519,148; dated Jun. 8, 2018; pp. 1-12; Published: EP.
European Patent Office; "Extended European Search Report from EP Application No. 17207050.0 dated Apr. 20, 2018" from Foreign Counterpart of U.S. Appl. No. 14/357,917; pp. 1-6; dated Apr. 20, 2018; Published: EP.
International Bureau, "International Preliminary Report on Patentability from PCT Application No. PCT/CA2012/050808 dated May 20, 2014", from Foreign Counterpart to U.S. Appl. No. 14/357,917, dated May 20, 2014, pp. 1-6, Published: Switzerland.
International Searching Authority, "International Search Report and Written Opinion from PCT Application No. PCT/US2017/055442 dated Dec. 11, 2017", dated Dec. 11, 2017, pp. 1-14, Published: US.
IP Australia, "Notice of acceptance for patent application from AU Application No. 2015333623 dated Jul. 20, 2018", from Foreign Counterpart to PCT Application No. PCT/US2015/055441, dated Jul. 20, 2018, pp. 1-3, Published: AU.
IP Australia, "Notice of Acceptance from AU Application No. 2012339536 dated Jan. 28, 2016", from Foreign Counterpart to PCT Application No. PCT/CA2012/050808, dated Jan. 28, 2016, pp. 1-3, Published: AU.
IP Australia; "Examination report No. 1 for standard patent application from AU Application No. 2015333623 dated Sep. 26, 2017"; from Foreign Counterpart of U.S. Appl. No. 15/519,148; dated Sep. 26, 2017; pp. 1-4; Published: AU.
Japanese Patent Office, "Decision to Grant from JP Application No. 2017519539 dated Jul. 31, 2018", from Foreign Counterpart to PCT Application No. PCT/US2015/055441, dated Jul. 31, 2018, pp. 1-3, Published: JP.
Japanese Patent Office, "Office Action from JP Application No. 2017519539 dated Jan. 10, 2018", from Foreign Counterpart to PCT Application No. PCT/US2015/055441, dated Jan. 10, 2018, pp. 1-6, Published: JP.
State Intellectual Property Office of P.R. China, "Notification on Grant of the Patent Right for Invention from CN Application No. 2012800661802 dated Apr. 28, 2017", from Foreign Counterpart to PCT Application No. PCT/CA2012/050808, dated Apr. 28, 2017, pp. 1-3, Published: CN.
U.S Patent and Trademark Office; "Final Office Action"; U.S. Appl. No. 14/300,752; dated Jan. 12, 2018; pp. 1-18; Published: US.
U.S. Patent and Trademark Office, "Interview Summary" U.S. Appl. No. 14/727,576, dated Feb. 17, 2016, pp. 1-4, Published: US.
U.S. Patent and Trademark Office, "Interview Summary", U.S. Appl. No. 14/727,576, dated Jun. 14, 2016, pp. 1-3, Published: US.
U.S. Patent and Trademark Office, "Notice of Allowance" U.S. Appl. No. 14/727,576, dated Jul. 19, 2016, pp. 1-8, Published: US.
U.S. Patent and Trademark Office, "Office Action", U.S. Appl. No. 14/727,576, dated Oct. 16, 2015, pp. 1-14, Published: US.
U.S. Patent and Trademark Office, "Office Action", U.S. Appl. No. 14/727,576, dated Apr. 28, 2016, pp. 1-15, Published: US.
U.S. Patent and Trademark Office, "Restriction Requirement", U.S. Appl. No. 14/727,576, dated Jul. 23, 2015. pp. 1-10, Published: US.
U.S. Patent and Trademark Office, "Restriction Requirement", U.S. Appl. No. 15/285,811, dated Mar. 30, 2018, pp. 1-7, Published: US.
U.S. Patent and Trademark Office; "Office Action"; U.S. Appl. No. 15/519,148; dated Jul. 26, 2018; pp. 1-38; Published: US.
Novick, "Pelvic Fractures/Acetabular Fractures", Hospital for Special Surgery, Mar. 30, 2006, pp. 1-9, HSS.edu.

(56) References Cited

OTHER PUBLICATIONS

International Searching Authority, "International Search Report and Written Opinion from PCT Application No. PCT/CA2019/051471", dated Feb. 5, 2020, pp. 1-14, Published: WO.
European Patent Office, "Extended European Search Report from EP Application No. 17859233.3", from Foreign Counterpart to U.S. Appl. No. 16/340,067, dated Apr. 23, 2020, pp. 1 through 8, Published: EP.
U.S. Patent and Trademark Office, "Office Action", U.S. Appl. No. 16/384,758, dated Jul. 24, 2020, pp. 1 through 69, Published: US.
U.S. Patent and Trademark Office, "Office Action", U.S. Appl. No. 16/414,435, dated Jul. 14, 2020, pp. 1 through 62, Published: US.
U.S. Patent and Trademark Office, "Notice of Allowance", U.S. Appl. No. 16/384,758, dated Dec. 2, 2020, pp. 1 through 21, Published: US.
U.S. Patent and Trademark Office, "Restriction Requirement", U.S. Appl. No. 16/340,067, dated Dec. 16, 2020, pp. 1 through 7, Published: US.
European Patent Office, "Communication pursuant to Article 94(3) EPC from Application No. 15850096.7", from Foreign Counterpart to U.S. Appl. No. 15/519,148, dated Sep. 21, 2020, pp. 1 through 4, Published: EP.
European Patent Office, "Communication pursuant to Article 94(3) EPC from EP Application No. 17207050.0", from Foreign Counterpart to U.S. Appl. No. 14/357,917, dated Aug. 26, 2020, pp. 1 through 3, Published: EP.
International Bureau, "International Preliminary Report on Patentability from PCT Application No. PCT/CA2019/051471", from Foreign Counterpart to U.S. Appl. No. 17/286,388, dated Apr. 29, 2021, pp. 1 through 9, Published: WO.
U.S. Patent and Trademark Office, "Final Office Action", U.S. Appl. No. 16/414,435, dated Mar. 22, 2021, pp. 1 through 26, Published: US.
U.S. Patent and Trademark Office, "Advisory Action", U.S. Appl. No. 16/414,435, dated Aug. 24, 2021, pp. 1 through 4, Published: US.
U.S. Patent and Trademark Office, "Office Action", U.S. Appl. No. 16/340,067, dated Oct. 4, 2021, pp. 1 through 97, Published: US.
European Patent Office, "Communication pursuant to Article 94(3) EPC from EP Application No. 15850096.7", from Foreign Counterpart to U.S. Appl. No. 15/519,148, dated Oct. 5, 2021, pp. 1 through 5, Published: EP.

* cited by examiner

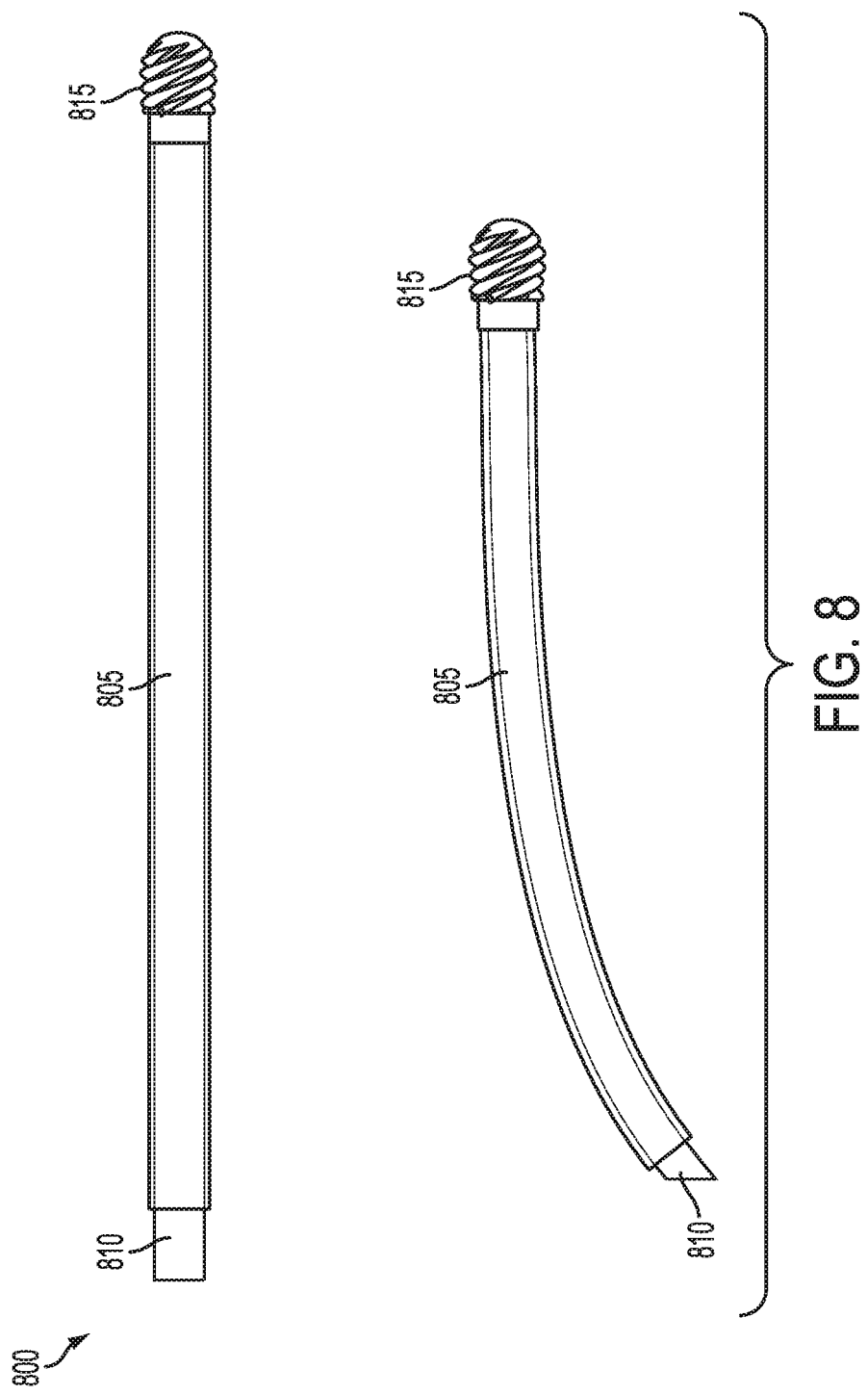

INTRAMEDULLARY FIXATION SYSTEM FOR MANAGEMENT OF PELVIC AND ACETABULAR FRACTURES

CROSS-REFERENCE TO RELATED APPLICATIONS

This application is a continuation of U.S. patent application Ser. No. 14/300,752, filed Jun. 10, 2014, which is a continuation of U.S. patent application Ser. No. 14/357,917, filed on May 13, 2014, now U.S. Pat. No. 9,839,435, which is the U.S. National Stage Entry of International Application Serial No. PCT/CA2012/050808, filed Nov. 14, 2012, which claims benefit of U.S. Provisional Patent Application Ser. No. 61/559,609, filed Nov. 14, 2011, which are incorporated in their entirety herein by reference.

BACKGROUND

FIG. 1A depicts a frontal view of the skeletal structure forming the pelvic ring, and FIGS. 1B and 1C depict cross-sectional side views of the skeletal structure forming the pelvic ring. As shown in FIGS. 1A, 1B and 1C, the pelvic ring includes right and left ilium bones 105, 110, the sacrum 115 and their associated ligamentous connections. The main connections are through and around the right and left sacroiliac joints 120, 125 at the posterior of the pelvis and the pubic symphysis 130 at the anterior of the pelvis. The pelvic ring is a key structural element of the skeletal system because it is a weight-bearing structure interposed between the upper body and the legs. As such, if a fracture occurs and it is untreated, the pelvic ring may not heal (nonunion) or may heal in a poor position (malunion). Nonunion can lead to chronic pain and an inability to walk. Malunion can result in a short leg or one which points in the wrong direction. Because of these problems, it is necessary to reposition to normal the fragments which have become displaced during the fracturing (reduction). Once the fragments are repositioned, it is necessary to hold them in place (fixation) until the healing of the fracture is complete. This process may take approximately 6 to 8 weeks.

Because the pelvic ring forms a ring structure, it cannot be disrupted in one place when a fracture occurs. Typically, a disruption, or "break," occurs in both the posterior and anterior portions of the pelvic ring. The disruptions in the pelvic ring can be through one or more of the bones 105, 110, 115, through the posterior sacroiliac joints 120, 125, through the pubic symphysis 130 at the front, or any number of combinations of the above. If the acetabulum (a portion of each ilium bone 105, 110 forming the hip socket) is fractured, the smooth bearing surface of the acetabulum must be restored to as close to its original shape as possible in order to allow for proper movement at the hip. Once restored, the acetabulum must be held in the restored position until healing occurs.

Conventional treatment of a pelvic fracture includes reduction of the fracture fragments and fixation with plates and screws along the surface of the bone. However, placing a plate on the bone requires a significant operation with resulting high blood loss. In some cases, a straight intramedullary screw may be placed along a curved path. While the screw is less invasive, the fixation may be inadequate because the straight screw cannot be implanted very far into a curved bone. This may result in inadequate fixation. Moreover, the screw must be relatively small in diameter to avoid extending through the bone. Surgically speaking, implanting a screw such that it extends from the bone can result in significant hazard to the patient because it may puncture or otherwise impinge upon important vascular and nervous structures.

SUMMARY

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In an embodiment, a device for treating a fracture of a bone may include a flexible tube having a distal end and a proximal end, a stiffening mechanism within the flexible tube configured to cause the flexible tube to become rigid, and an actuator configured to cause the stiffening mechanism to cause the flexible tube to become rigid in response to the actuator being actuated.

In an embodiment, a method of treating a fracture of a bone may include inserting a guide wire including a bent section having a sharpened tip at a distal portion of the guide wire into an intramedullary space of the bone, forming a tunnel surrounding the guide wire in the bone, inserting a flexible device into the tunnel, and causing the flexible device to become rigid in the tunnel in order to fix a fracture of the bone.

In an embodiment, a device for treating a fracture of a bone may include a flexible tube having a distal end and a proximal end, a plurality of rods contained within the flexible tube, and an actuator configured to cause the plurality of rods to be fixed in place when actuated.

In an embodiment, a device for treating a fracture of a curved bone may include a flexible tube having a distal end and a proximal end, a spring contained within the flexible tube, an actuator configured to cause the spring to exert a normal force against an inner surface of the flexible tube in response to the actuator being actuated.

In an embodiment, a kit may include a flexible device comprising a flexible tube having a distal end and a proximal end, and an actuator configured to cause the stiffening mechanism to cause the flexible tube to become rigid in response to the actuator being actuated, and instructions for using the flexible device to fix a bone fracture.

In an embodiment, a device for treating a fracture of a bone may include a flexible tube having a distal end and a proximal end and including a series of slits configured to allow the flexible tube to flex, a high helix angle screw positioned at the distal end of the flexible tube, a plurality of bead segments, including a distal bead segment and a proximal bead segment, within the flexible tube configured to cause the flexible tube to become rigid, wherein each of the plurality of bead segments comprises a distal end, a proximal end and a bore, a cannula extending through the bore of each of the plurality of bead segments and having a distal end connected to the distal bead segment and a proximal end extending from the proximal end of the flexible tube, and a cap connected to the proximal end of the flexible tube and configured to permit the flexible tube to be rotated.

In an embodiment, a device for treating a bone may include a plurality of bead segments including a distal bead segment and a proximal bead segment where each of the plurality of bead segments comprises a distal end, a proximal end and a bore, a screw head in contact with a distal end of the distal bead segment, a stiffening cable extending through the bore of each of the plurality of bead segments, and a tensioning assembly in contact with a proximal end of the proximal bead segment. The tensioning assembly may be configured to cause the stiffening cable to cause the proximal end of each bead segment to engage a distal end of an adjacent bead segment. The stiffening cable may have a distal end connected to the screw head and a proximal end connected to the tensioning assembly.

BRIEF DESCRIPTION OF THE FIGURES

FIG. 8 depicts an alternate exemplary device for treating a bone according to an embodiment.

DETAILED DESCRIPTION

The following term shall have, for the purposes of this application, the meaning set forth below.

The terms "fixing" or "to fix" refer to holding or setting something in place. In particular, a bone fracture may be fixed by causing a device placed across the point of fracture to become rigid, thereby stabilizing the bone on either side of the fracture. Additionally, the device itself may become fixed by making the device become rigid as a result of actuation of an actuator.

Figure 1A:
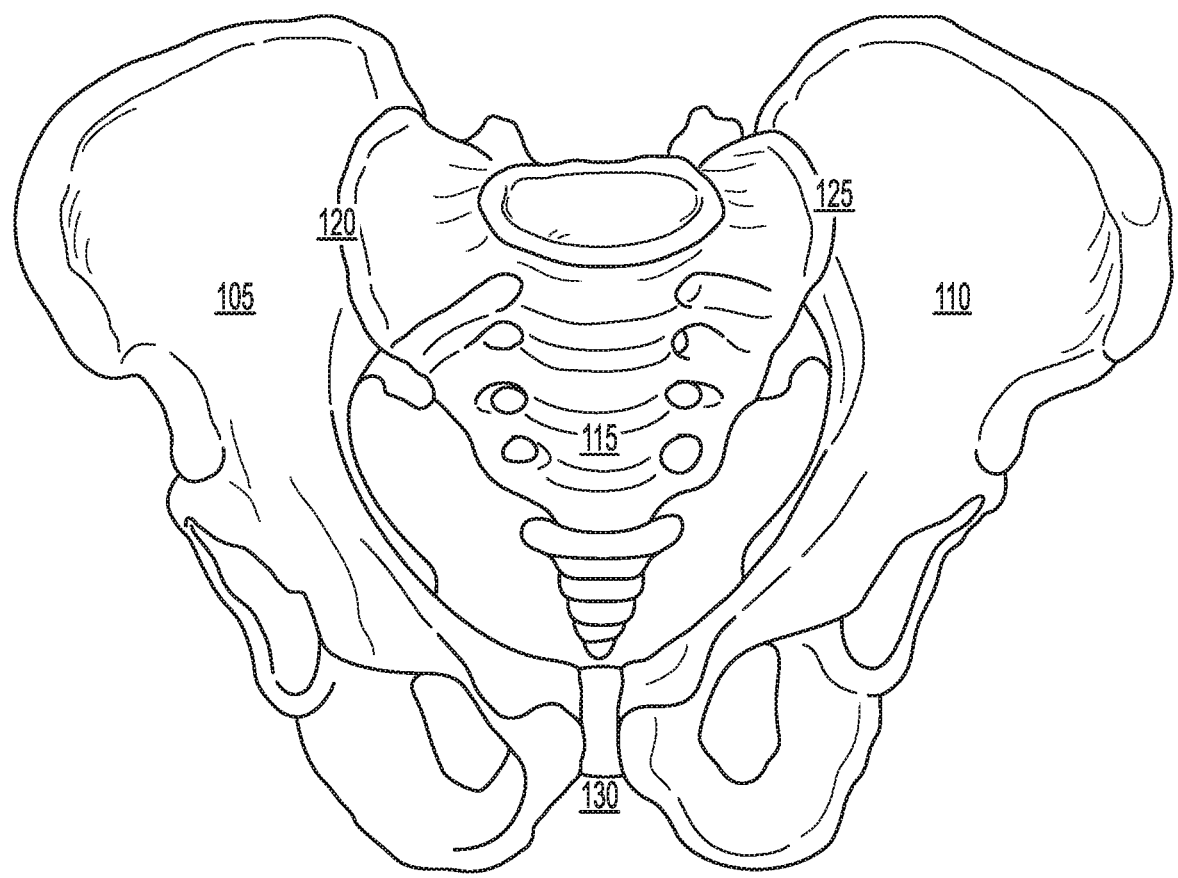
FIG. 1A depicts a frontal view of the skeletal structure forming the pelvic ring.
Figure 1B:
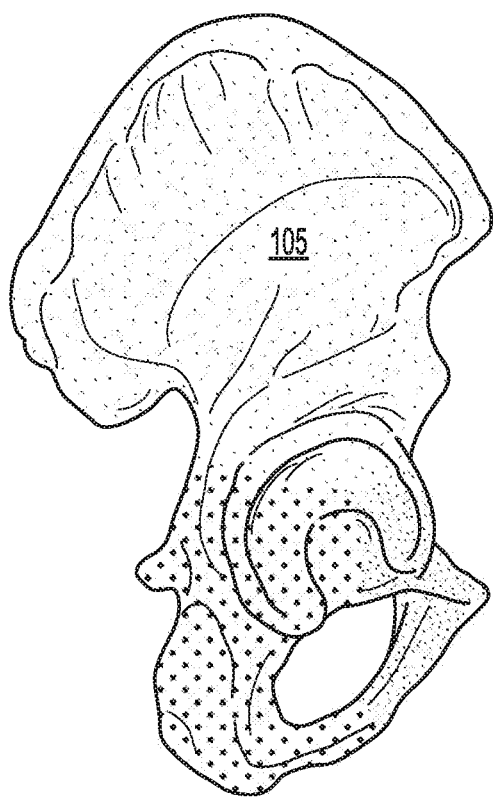
FIGS. 1B and 1C depict cross-sectional side views of the skeletal structure forming the pelvic ring.
Figure 1C:
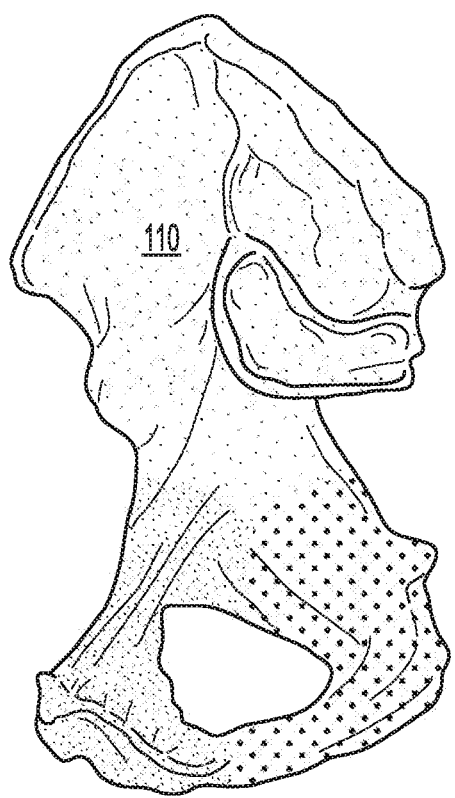
Figure 2A:
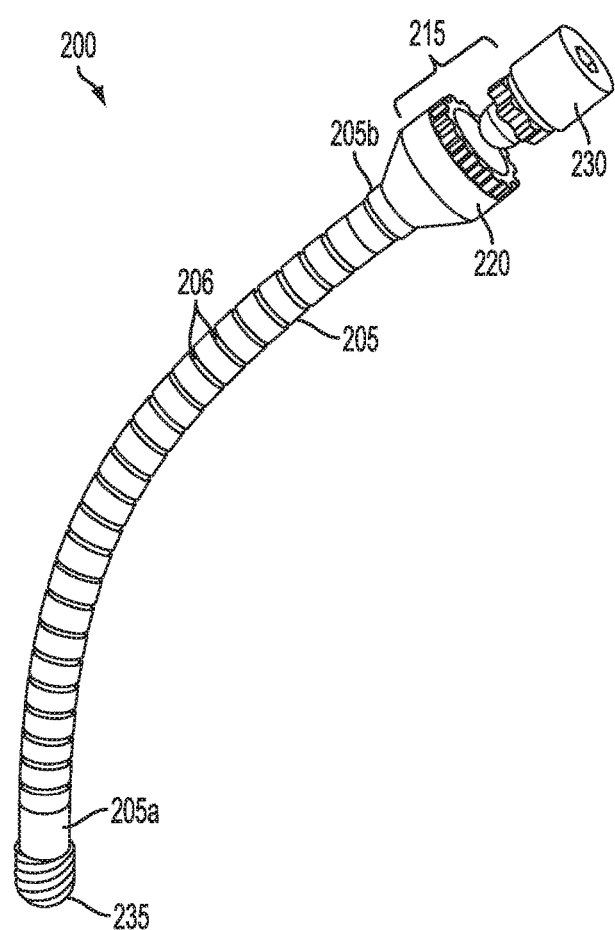
FIG. 2A depicts an exemplary device for treating a bone according to an embodiment.
Figure 2B:
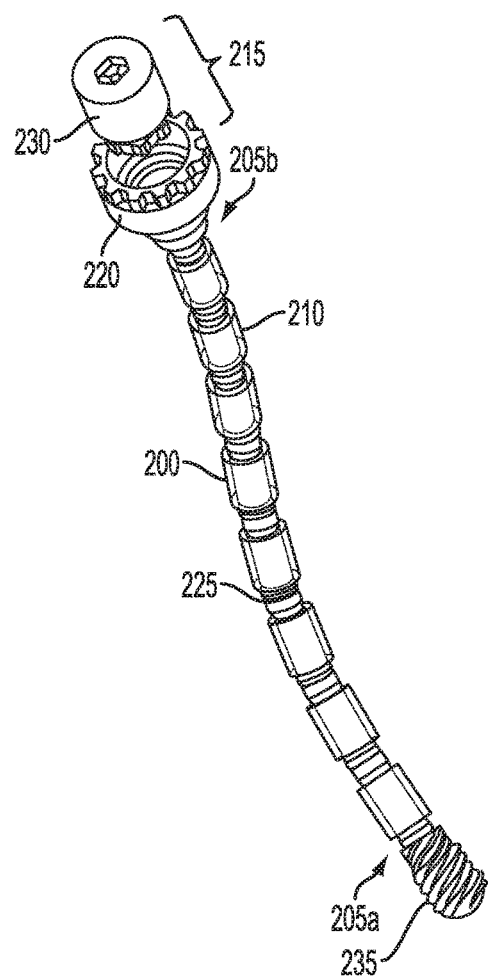
FIG. 2B depicts interior portions of the exemplary device of FIG. 2A according to an embodiment.

FIG. 2A depicts an exemplary device for treating a bone according to an embodiment. FIG. 2B depicts interior portions of the exemplary device according to an embodiment. As shown in FIGS. 2A and 2B, the device 200 may include a flexible tube 205, a stiffening mechanism 210 and an actuator 215. The flexible tube 205 may have a distal end 205a and a proximal end 205b. The flexible tube 205 may include a plurality of slits, such as 206, in an outer housing configured to allow the flexible tube to flex. In an embodiment, the flexible tube 205 may comprise stainless steel and/or nitinol.

The stiffening mechanism 210 may be located within the flexible tube 205 and may be configured to cause the flexible tube to become rigid. In an embodiment, the stiffening mechanism 210 may include a plurality of expansion sleeves. Exemplary expansion sleeves are disclosed in FIGS. 3-5 and are discussed in further detail below.

Figure 3:
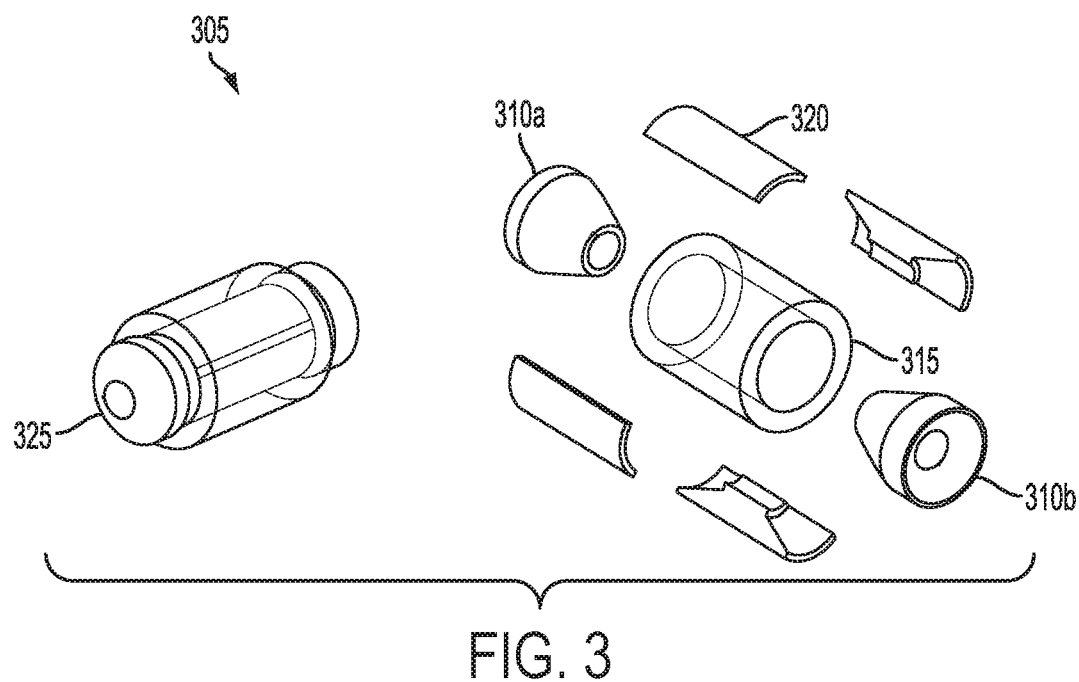
FIG. 3 depicts an exemplary expansion sleeve according to an embodiment.

FIG. 3 depicts an exemplary expansion sleeve according to an embodiment. As shown in FIG. 3, the expansion sleeve may include a jam nut 305 having expansion beads 310a and 310b, cladding 315 covering at least a portion of the expansion beads, a plurality of expanding segments, such as 320, and a bore 325. The jam nut 305 may include an expansion bead 310a having a convex end and an expansion bead 310b having a concave end. Each of the expansion beads 310a and 310b may taper down in diameter from the convex/concave end to the other end of the bead. The convex expansion bead 310a of a first expansion sleeve and the concave expansion bead 310b of a second adjacent expansion sleeve are configured to enable the adjacent expansion sleeves to abut each other when the actuator 215 is actuated. The cladding 315 may be made of, for example and without limitation, silicone and may provide some compliance when the expansion sleeve 305 contacts the interior surface of the flexible tube 205. The jam nut 305 may be actuated by causing the expansion beads 310a and 310b to be moved towards each other causing the cladding 315 to expand. As such, the expanding segments 320 may be configured to be in a non-actuated state against the cladding 315 when the jam nut 305 is not actuated. In contrast, when the jam nut 305 is actuated, the cladding 315 may force the expanding segments 320 to abut an interior surface of the flexible tube 205. As such, the expanding segments 320 may cause the flexible tube 205 to become rigid when the jam nut 305 is in an actuated state. The bore 325 may be configured to receive a cannula, as discussed below.

Figure 4:
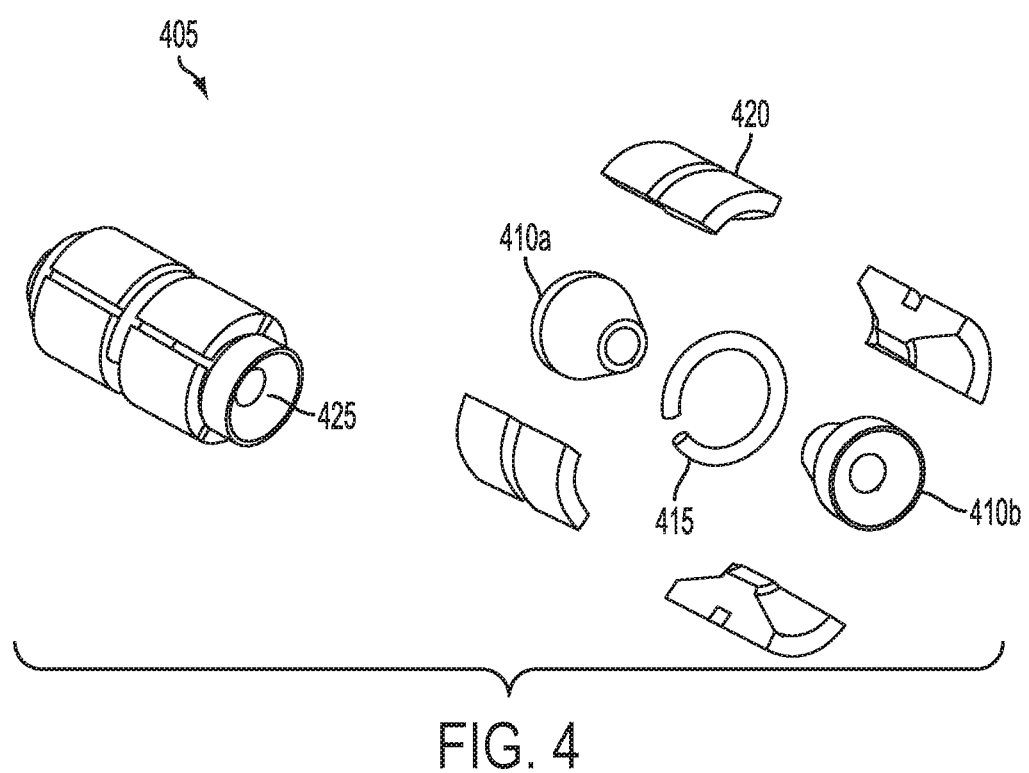
FIG. 4 depicts an alternate exemplary expansion sleeve according to an embodiment.

FIG. 4 depicts an alternate exemplary expansion sleeve according to an embodiment. As shown in FIG. 4, expansion sleeve 405 may include expansion beads 410a and 410b, a retaining spring 415, a plurality of expanding segments, such as 420, and a bore 425. The expansion sleeves may include an expansion bead 410a having a convex end and an expansion bead 410b having a concave end. Each of the expansion beads 410a and 410b may taper down in diameter from the convex/concave end to the other end of the bead. The convex expansion bead 410a of a first expansion sleeve and the concave expansion bead 410b of a second adjacent expansion sleeve are configured to enable the adjacent expansion sleeves to abut each other when the actuator 215 is actuated. The retaining spring 415 may provide some compliance when the expansion sleeve 405 contacts the interior surface of the flexible tube 205. The expansion sleeve 405 may be actuated by causing the expansion beads 410a and 410b to be moved towards each other causing the expanding segments 420 to be pushed towards an inner surface of the flexible tube 205. As such, the retaining spring 415 may be configured to restrain the expanding segments 420 when in a non-actuated state. In contrast, when the actuator 215 is actuated, the expanding segments 420 may be configured to abut an interior surface of the flexible tube 205. In this way, the expanding segments 420 may cause the flexible tube 205 to become rigid when in an actuated state. The bore 425 may be configured to receive a cannula, as discussed below.

Figure 5:
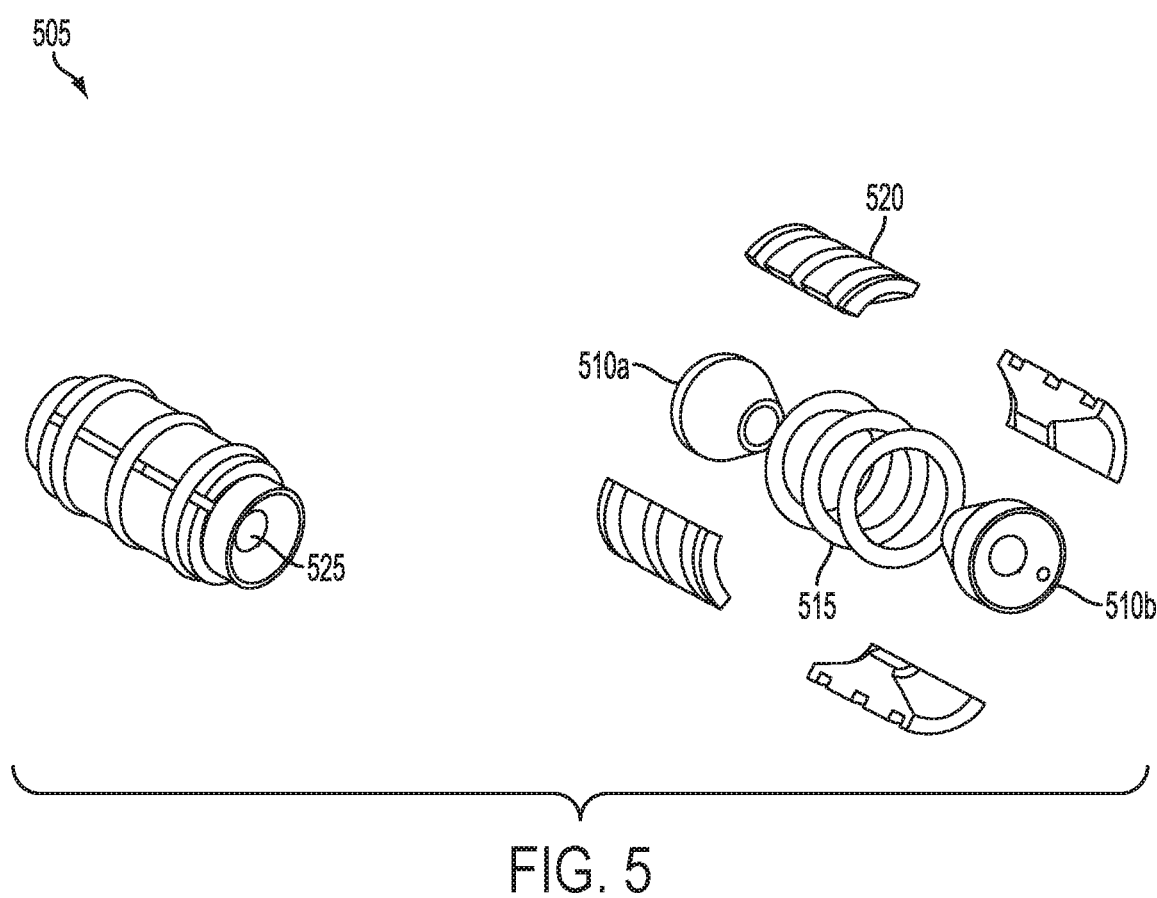
FIG. 5 depicts an alternate exemplary expansion sleeve according to an embodiment.

FIG. 5 depicts an alternate exemplary expansion sleeve according to an embodiment. As shown in FIG. 5, expansion sleeve 505 may include expansion beads 510a and 510b, one or more O-rings 515, a plurality of expanding segments, such as 520, and a bore 525. The expansion sleeves may include an expansion bead 510a having a convex end and an expansion bead 510b having a concave end. Each of the expansion beads 510a and 510b may taper down in diameter from the convex/concave end to the other end of the bead. The convex expansion bead 510a of a first expansion sleeve and the concave expansion bead 510b of a second adjacent expansion sleeve are configured to enable the adjacent expansion sleeves to abut each other when the actuator 215 is actuated. The one or more O-rings 515 may provide some compliance when the expansion sleeve 505 contacts the interior surface of the flexible tube 205. The expansion sleeve 505 may be actuated by causing the expansion beads 510a and 510b to be moved towards each other causing the expanding segments 520 to be pushed towards an inner surface of the flexible tube 205. As such, the one or more Orings 515 may be configured to restrain the expanding segments 520 when in a non-actuated state. In contrast, when the actuator 215 is actuated, the expanding segments 520 may be configured to abut an interior surface of the flexible tube 205. As such, the expanding segments 520 may cause the flexible tube 205 to become rigid when in an actuated state. The bore 525 may be configured to receive a cannula, as discussed below.

The expansion sleeves discussed in FIGS. 3-5 are exemplary and are not meant to be limiting. Additional and/or alternate devices for forming expansion sleeves may be used within the scope of this disclosure.

Referring back to FIG. 2, the actuator 215 may be configured to cause the stiffening mechanism 210 to cause the flexible tube 205 to become rigid in response to the actuator being actuated. In an embodiment, the actuator 215 may include, for example and without limitation, a cap 220 connected to the proximal end of the flexible tube 205. In an embodiment, the cap 220 may be configured to permit the flexible tube 205 to be rotated, thereby allowing the flexible tube to be inserted into a bone. The cap 220 may also be configured to cause the stiffening mechanism 210 to become rigid. For example, if the stiffening mechanism 210 comprises a plurality of expansion sleeves, the cap 220, when rotated, may be configured to cause each of the plurality of expansion sleeves to abut an interior surface of the flexible tube 205.

In an alternate embodiment, the actuator 215 may include a cannula 225 with a locking assembly 230. The cannula 225 may extend through a bore in each of a plurality of expansion sleeves, such as 305, 405 or 505. The cannula 225 may include a distal end connected to a distal expansion sleeve located at the distal end of the flexible tube 205 and a proximal end extending from the proximal end of the flexible tube. In an embodiment, the cannula 225, when actuated, may cause the plurality of expansion sleeves 305, 405 or 505 to actuate, which may cause the flexible tube 205 to become rigid, as described above. The locking assembly 230 may be used to actuate the cannula 225. For example, the locking assembly 230 may cause the cannula 225 to become tensioned. The locking assembly 230 may then be used to lock the cannula 225 in the actuated state.

Figure 6:
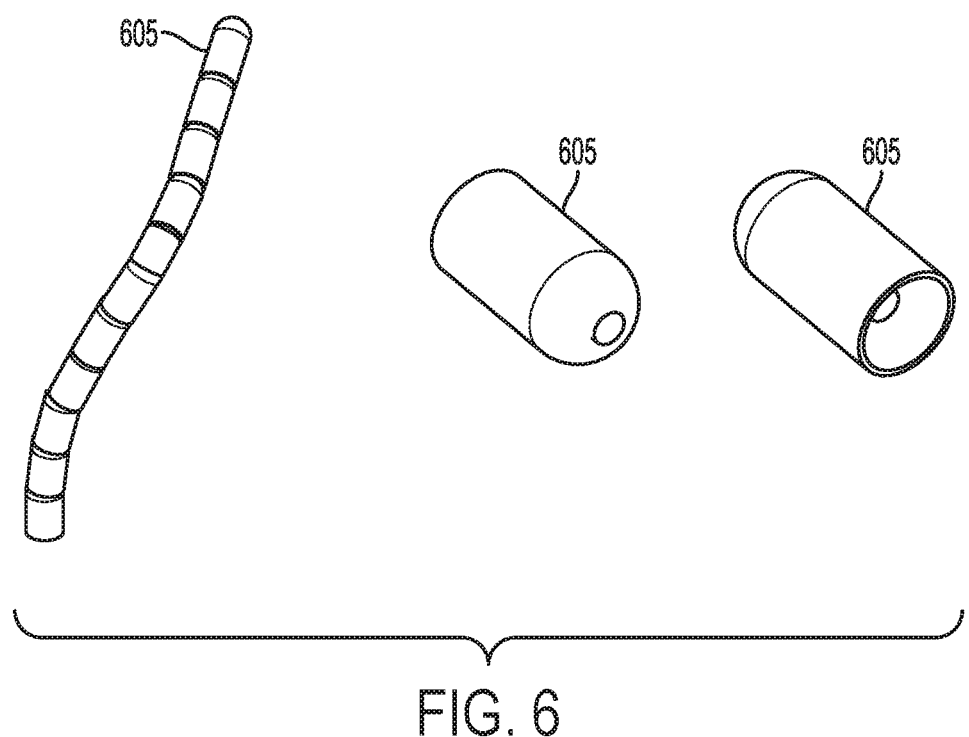
FIG. 6 depicts an exemplary bead segment and flexible device incorporating a plurality of bead segments according to an embodiment.

In an alternate embodiment, the cannula 225 may extend through a bore in each of a plurality of bead segments, such as 605 in FIG. 6. Each of the bead segments 605 may further include a distal end and a proximal end. In an embodiment, the distal end of a bead segment 605 may be sized and shaped to be received by, receive or otherwise engage a proximal end of an adjacent bead segment in response to the cannula 225 being actuated. For example, the distal end of each bead segment 605 may be convex, and the proximal end of each bead segment may be concave. Conversely, the distal end and proximal end of each bead segment 605 may be concave and convex, respectively. Additional or alternate shapes for the distal and proximal ends of bead segments 605 may be used within the scope of this disclosure.

In an embodiment, each of the bead segments 605 may be about 8 mm in diameter and about 12 mm in length. In an embodiment, each of the bead segments 605 may be about 2 mm to about 15 mm in diameter. In an embodiment, each of the bead segments 605 may be about 5 mm to about 25 mm in length. Alternately sized bead segments 605 may also be used within the scope of this disclosure.

The cannula 225 may include a distal end connected to a distal bead segment located at the distal end of the flexible tube 205 and a proximal end extending from the proximal end of the flexible tube. In an embodiment, the cannula 225, when actuated, may cause the plurality of bead segments 605 to actuate, which may cause the flexible tube 205 to become rigid. The locking assembly 230 may be used to actuate the cannula 225. For example, the locking assembly 230 may cause the cannula 225 to become tensioned. The locking assembly 230 may then be used to lock the cannula 225 in the actuated state.

In an embodiment, a screw 235 may additionally be positioned at the distal end of the flexible tube 205. The screw 235 may be used to enable the flexible tube 205 to be inserted into a bone. In an embodiment, the screw 235 may be a high helix angle screw. In an embodiment, the screw 235 may move a distance into a medium, such as a bone, that is approximately equal to its diameter when rotated one revolution. In other words, a screw 235 having a diameter of 12 mm may move forward approximately 12 mm when rotated once.

Figure 13:
FIG. 13 depicts an exemplary guide wire according to an embodiment.

FIG. 13 depicts an exemplary guide wire 1300. The guide wire may include a bent section 1305 having a sharpened tip 1310 at a distal portion 1315.

Figure 7:
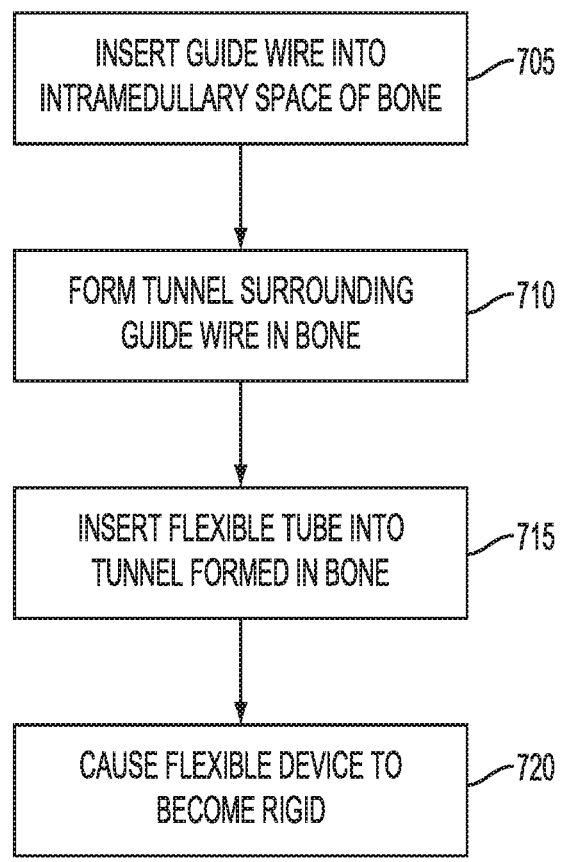
FIG. 7 depicts a flow diagram for an exemplary method of treating a bone according to an embodiment.

FIG. 7 depicts a flow diagram for an exemplary method of treating a bone according to an embodiment. As shown in FIG. 7, a guide wire may be inserted 705 into an intramedullary space of a bone. An exemplary guide wire is shown in FIG. 13. Referring now to FIG. 13, the guide wire 1300 may include a bent section 1305 having a sharpened tip 1310 at a distal portion of the guide wire 1315. The guide wire may be inserted 705 by rotating the guide wire to orient the bent section 1305 of the guide wire and selectively hammering the guide wire to cause the bent section to form a curved path in bone based on the orientation of the bent section. In an embodiment, inserting 705 the guide wire 1300 may include using a fluoroscope to determine the orientation of the bent section 1305 of the guide wire. In an embodiment, the guide wire 1300 may be attached to a hammer drill during insertion 705. During insertion of the guide wire 1300, a user may orient the bent tip 1305 so that it is positioned in the direction that the guide wire is to be inserted 705. The hammer drill may then be activated to cause the guide wire 1300 to be inserted into the bone in such direction. In particular, the sharpened tip 1310 may be used to cause the hole to be formed in the bone. If the user determines that the direction of insertion 705 for the guide wire 1300 is to be changed, the guide wire may be reoriented prior to further insertion of the guide wire. In an embodiment, a straight path may be approximated by inserting the guide wire 1300 in a succession of short curved paths that are substantially 180 degrees opposed to each other. As such, although the present method may be used to insert a guide wire 1300 into curved bone, such as at least a portion of a pelvic ring, a posterior column of an acetabulum or an anterior column of an acetabulum of a patient, the method may also be used to insert a guide wire into a substantially straight bone as well.

In an embodiment, the guide wire 1300 may include one or more of stainless steel and nitinol. In an embodiment, the guide wire 1300 may be about 1 mm to about 1.5 mm in diameter. It will be apparent to those of ordinary skill in the art that the guide wire 1300 may be of a different size depending upon the particular bone into which the guide wire is to be inserted and that the disclosed size range is merely exemplary.

A tunnel may be formed 710 surrounding the guide wire 1300 in the bone. In an embodiment, the tunnel may be formed 710 using a cannulated reamer with a flexible drive shaft that fits over and around the guide wire 1300. The cannulated reamer may include a bore configured to receive the guide wire 1300. As such, the guide wire 1300 may guide the direction of the cannulated reamer in forming 710 the space in the bone.

The cannulated reamer may be configured to have a diameter sufficient to allow a flexible device, such as at least one of the flexible tubes described in reference to FIGS. 2, 6 and 8, to be inserted 715 into the tunnel. In an embodiment, the cannulated reamer may be short enough to enable the reamer to form and follow a curved hole defined by the guide wire.

The flexible device may be caused 720 to become rigid when in the tunnel. In particular, the rigid flexible device may be used to treat a bone fracture. In an embodiment, the flexible device may be caused 720 to become rigid by operating an actuator and, in response to operating the actuator, rigidizing the flexible device from a flexible state to a more rigid state. For example, expansion sleeves, jam nuts and/or bead segments described above in reference to FIGS. 3-6 may be used to abut against an interior surface of the flexible device causing the flexible device to hold its shape when actuated. In an embodiment, the expansion sleeves may include one or more of a spring, one or more jam nuts and one or more O-rings. In an embodiment, a flexible device may be caused 720 to become rigid by actuating a cannula extending through each of a plurality of expansion sleeves. In an alternate embodiment, a flexible device may be caused 720 to become rigid by rotating a cap located at a proximal end of the flexible device.

FIG. 8 depicts an alternate exemplary device for treating a bone according to an embodiment. As shown in FIG. 8, the device 800 may include a flexible tube 805, a plurality of rods 810 contained within the flexible tube, and an actuator (not shown). The flexible tube 805 may include a distal end and a proximal end. In an embodiment, the flexible tube 805 may include a series of slits configured to allow the tube to flex. In an embodiment, the flexible tube 805 may include stainless steel and/or nitinol.

In an embodiment, the plurality of rods 810 may be affixed to each other at the distal end of the flexible tube 805 and/or affixed to the distal end of the flexible tube. The plurality of rods 810 may substantially or completely fill the flexible tube 805 such that the rods cannot substantially move with respect to each other inside the flexible tube. In particular, the rods 810 remain parallel to each other and are constrained from deflecting in a radial direction. In an embodiment, the plurality of rods 810 move axially as the flexible tube 805 is flexed. As such, a rod 810 positioned along the inside of a curve traverses a shorter distance that a rod positioned along the outside of the curve, where the relative lengths of the rods change as the curve is modified.

The actuator may be configured to cause the plurality of rods to be fixed in place when actuated. In an embodiment, the actuator may be configured to cause the plurality of rods 810 to be fixed in place by causing the plurality of rods to lock in place at the proximal end of the flexible tube 805. If the plurality of rods 810 are locked together at the proximal end of the flexible tube 805, any curve(s) in the tube may be fixed in place.

In an embodiment, the device 800 may further include a screw 815 positioned at the distal end of the flexible tube 805. The screw 815 may be used to enable the flexible tube 805 to be inserted into a bone. In an embodiment, the screw 815 may be a high helix angle screw. In an embodiment, the screw 815 may move a distance into a medium, such as a bone, that is approximately equal to its diameter when rotated one revolution. In other words, a screw 815 having a diameter of 12 mm may move forward approximately 12 mm when rotated once.

In an embodiment, the device 800 may further include a sleeve (not shown) located within the flexible tube 805. The sleeve may be configured to contain the plurality of rods 810. In an embodiment, the actuator may be configured to cause the plurality of rods 810 to be fixed by causing the sleeve to apply a normal force towards a center of the sleeve in response to the actuator being actuated. As such, the sleeve may compress the plurality of rods 810 causing the rods to be incapable of movement, thereby causing the flexible tube 805 to become rigid.

In an embodiment, a device for treating a bone may include a flexible tube similar to one of the flexible tubes described above, a spring contained within the flexible tube and an actuator configured to cause the spring to exert a normal force against an inner surface of the flexible tube in response to the actuator being actuated. The normal force exerted by the spring may cause the flexible tube to become rigid. The flexible tube may include a series of slits configured to allow the tube to flex. The flexible tube may include stainless steel and/or nitinol. In an embodiment, a screw may be positioned at the distal end of the flexible tube.

In an embodiment, a bone-treating device may be manufactured in the following manner or by performing similar operations. A flexible tube may be formed of a flexible material, such as super-elastic nitinol or spring-tempered stainless steel. The flexible tube may include a plurality of slits to allow the tube to be axially flexible, but stiff in torsion. Alternately, a gooseneck wound spring may be used. In an embodiment, a screw may be attached to a distal end of the flexible tube, and a cap may be attached to a proximal end of the flexible tube. The cap may include a structure that permits the cap to be turned by a wrench.

A stiffening system is inserted into the flexible tube such that a distal end of the stiffening system is attached to a distal end of the flexible tube. The stiffening system includes a cannula connected at a distal end to the distal end of the flexible tube and a plurality of bead segments or expansion sleeves threaded along the cannula. Each of the bead segments or expansion sleeves includes a bore permitting the cannula to pass therethrough. The bead segments and expansion sleeves are described in greater detail in reference to FIGS. 3-6.

Alternately, the stiffening system includes a plurality of thin rods attached at a distal end of the flexible tube. In an embodiment, the thin rods may be inserted inside of a sleeve surrounding the thin rods that is configured to prevent the rods from moving when actuated. Alternately, the stiffening system may include a lock at the proximal end of the flexible tube that is used to lock the thin rods in place.

In an embodiment, a bone containing a device for treating the bone may include the bone, and a device comprising a tube having a distal end and a proximal end, a stiffening mechanism configured to cause the tube to remain in a rigid state. In an embodiment, the device may include a screw positioned at the distal end of the tube.

In an embodiment, the stiffening mechanism may include a plurality of bead segments including a distal bead segment. Each of the plurality of bead segments may include a distal end and a proximal end. The distal end of each bead segment of the plurality of bead segments, other than the distal bead segment, may receive the proximal end of an adjacent bead segment of the plurality of bead segments. In an embodiment, each of the bead segments may be about 8 mm in diameter and about 12 mm in length. In an embodiment, each of the bead segments may be about 2 mm to about 15 mm in diameter. In an embodiment, each of the bead segments may be about 5 mm to about 25 mm in length. Alternately sized bead segments may also be used within the scope of this disclosure.

In an alternate embodiment, the stiffening mechanism may include a plurality of expansion sleeves. An expansion sleeve may include, for example and without limitation, a spring, one or more jam nuts, and/or one or more O-rings.

The above-described devices and methods may be used to treat a bone fracture. For example, bone fragments at the point of a fracture may be repositioned into a proper alignment, and a device, such as one described above, may be inserted in order to fix the bone fracture to allow healing to complete.

Alternately, the above-described devices and methods may be used to prophylactically treat a bone in order to provide support. For example, a metastatic tumor may cause a weak spot in a bone. A device may be inserted to provide support for such a weak spot. As another example, a device may be inserted to support the posterior and anterior columns of the acetabulum for the management of a complex total hip replacement procedure or a revision of a previous total hip replacement. Additional uses of the devices and methods described herein may also be performed within the scope of this disclosure.

Figure 9B:
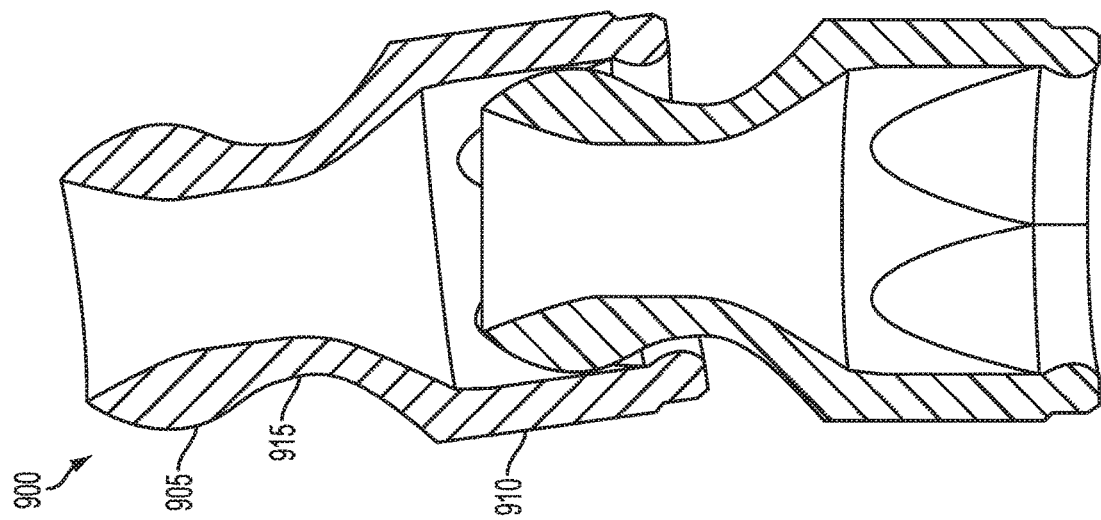
FIGS. 9A and 9B depict an external view and a cut-away view, respectively, of exemplary bead segments according to an embodiment.
Figure 9A:
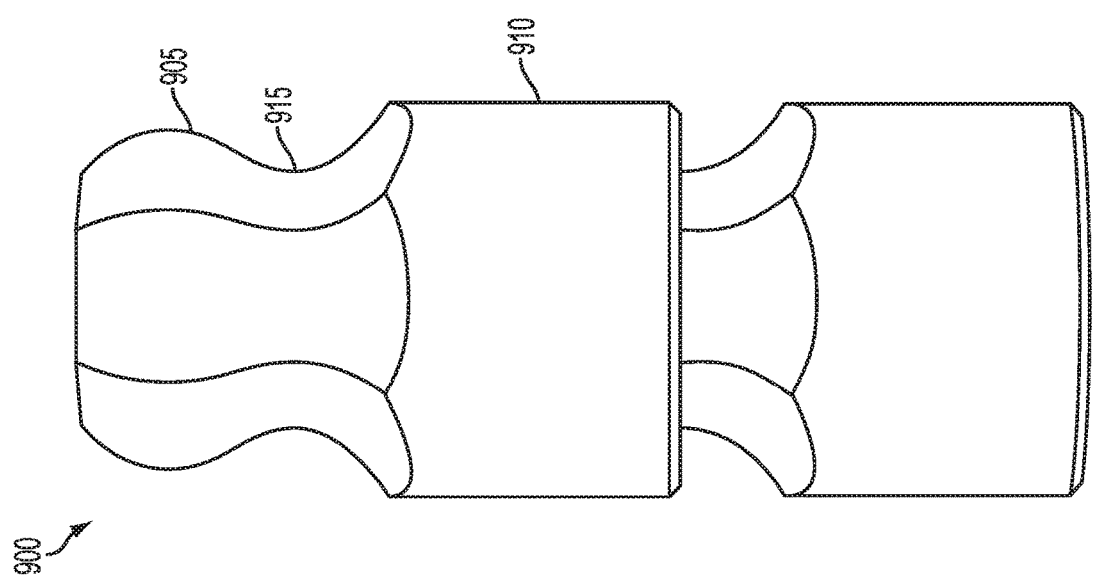

In an alternate embodiment, a device without a flexible tube may be manufactured for use as described above. FIGS. 9A and 9B depict an external view and a cut-away view, respectively, of exemplary bead segments according to an embodiment. As shown in FIGS. 9A and 9B, the bead segments, such as 900, may include a male surface 905 and a female (hollow) surface 910 and a bore. The bore of each bead segment may be configured to receive a stiffening cable or cannula as described above in reference to FIGS. 3-6.

The male surface 905 and the female surface 910 may have a shape that permits torque transfer from one bead segment to the next. For example, the male surface 905, and the female surface 910 may have a spherical and at a proximal end and a conical cross-section at a distal end, as described further below in reference to FIGS. 10A-D. Alternate cross-sectional shapes may also be used for the male surface 905 and the female surface 910 within the scope of this disclosure. For example, other multisided shapes, such as square cross-sections, pentagonal cross-sections, hexagonal cross-sections, heptagonal cross-sections, octagonal cross-sections, spherical cross-sections, conical cross-sections or the like, may be used within the scope of this disclosure.

Figure 11:
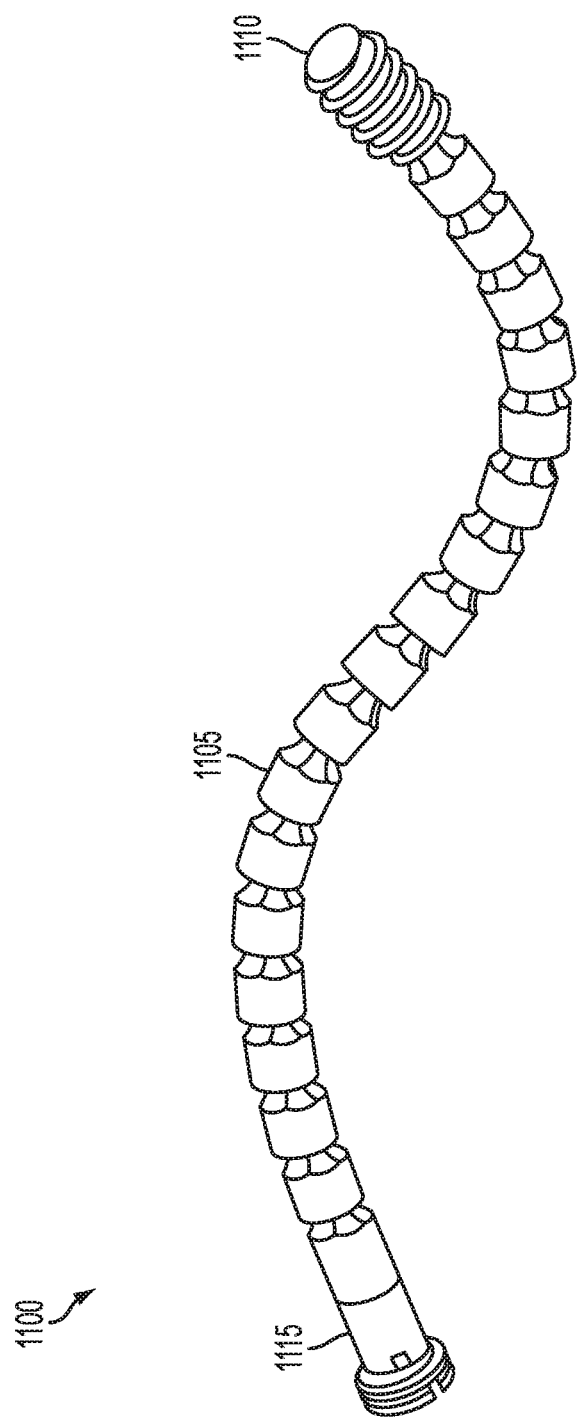
FIG. 11 depicts a flexible device incorporating a plurality of bead segments according to an embodiment.

The shapes of the male surface 905 and the female surface 910 of adjacent bead segments may permit torque to be transmitted from one bead to the next to drive a distal screw (such as 1110 in FIG. 11). In addition, the shapes of the male surface 905 and the female surface 910 of adjacent bead segments may enable the bead segments to pivot with respect to each other allowing the chain to form curved shapes.

The male surface 905 of each bead segment may include a narrowed neck 915 proximal to the ball to increase the bead-to-bead rotational angle. The narrowed neck 915 may further enable the open ends of the female surface 910 of an adjacent bead to be modified such that the male surface 905 of the bead cannot disengage. In an embodiment, the female surface 915 may be modified post-assembly in order to secure the connection. For example, a circlip may be added to a groove on the inside of the cavity of the female surface 915. Alternately, the edge of the female surface 915 may be crimped or rolled such that the inner diameter of the female surface is reduced at the edge. In this manner, a string of bead segments may be kept in an interlocked arrangement even if a central stiffening cable (not shown) is broken.

Figure 10A:
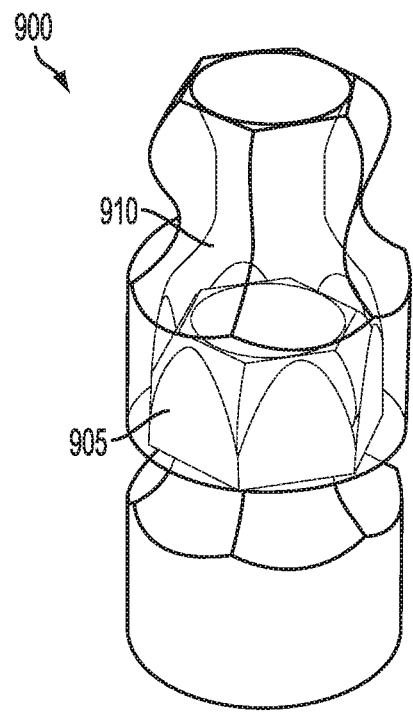
FIGS. 10A-D depict points of contact between the exemplary bead segments of FIGS. 9A and 9B.
Figure 10B:
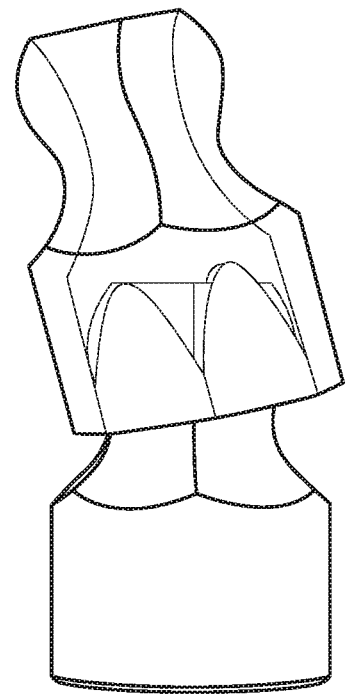
Figure 10C:
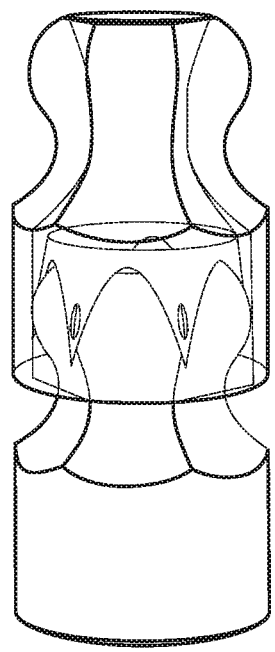
Figure 10D:
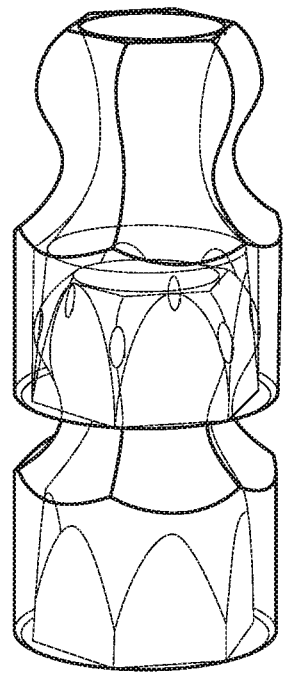

FIGS. 10A-D depict points of contact between the exemplary bead segments of FIGS. 9A and 9B. The male surface 905 and the female surface 910 of adjacent bead segments 900 have shapes that are capable of transmitting torque, such as hexagons. FIGS. 10A-D identify details of how the male surface 905 and the female surface 910 of the adjacent bead segments 900 interact. The female surface 910 may be substantially straightsided with a cross-section that is similar in nature to the male surface 905 of the adjacent bead segment 900. At the distal end of the female surface 910, a cone shape having a circular cross-section may be used. The corners of the male surface 905 of the adjacent bead segment 900 may make point contact with the cone-shaped portion of the female surface 910. This may cause localized points of high stress, which may lead to improved friction over line contact. In particular, the conical-shaped portion of the female surface 910 may permit improved friction as compared to a hexagonal prism because the hexagonal prism may not make even line contact around the male socket 905 as the adjacent bead segments 900 pivot with respect to each other. The described design may enable an interference fit, such as is shown in FIG. 10D, which may enable even higher friction as the point regions are distorted.

FIG. 11 depicts a flexible device incorporating a plurality of bead segments according to an embodiment. As shown in FIG. 11, the flexible device 1100 includes a plurality of bead segments, such as 1105, a distal screw 1110, a stiffening cable (not shown) inside the flexible device, and a tensioning assembly 1115. Each bead segment 1105 may be substantially similar to any of the bead segments identified herein or any other bead segment possessing similar characteristics to a bead segment identified within the scope of this disclosure, without limitation.

The stiffening cable may be a multi-stranded wire that passes through the bead segments 1105. The stiffening cable may be anchored at the distal screw 1110 at the distal end of the flexible device 1100 and at the tensioning assembly 1115 at a proximal end of the flexible device. In an embodiment, the stiffening cable may be anchored at each of the distal and proximal ends by thermal welding, soldering, gluing, welding a tapered collet in place or the like.

While the stiffening cable may be soldered to an anchor so that stress is distributed along an entire hole in which the stiffening cable is anchored such that the solder may wick throughout the hole, a mechanically suitable solder may not be biocompatible. In an embodiment, soldering the stiffening cable to a tapered collet may be used to avoid bioincompatibility within a patient. The collet may be fitted over a stiffening cable and then pressed into a conical hole, which distorts the collet into the cable. The collet may be welded in place at its outside edge so that the cable itself does not experience heating. In such an embodiment, the stiffening cable may receive substantially equal stress in each direction around the tapered collet.

Figure 12A:
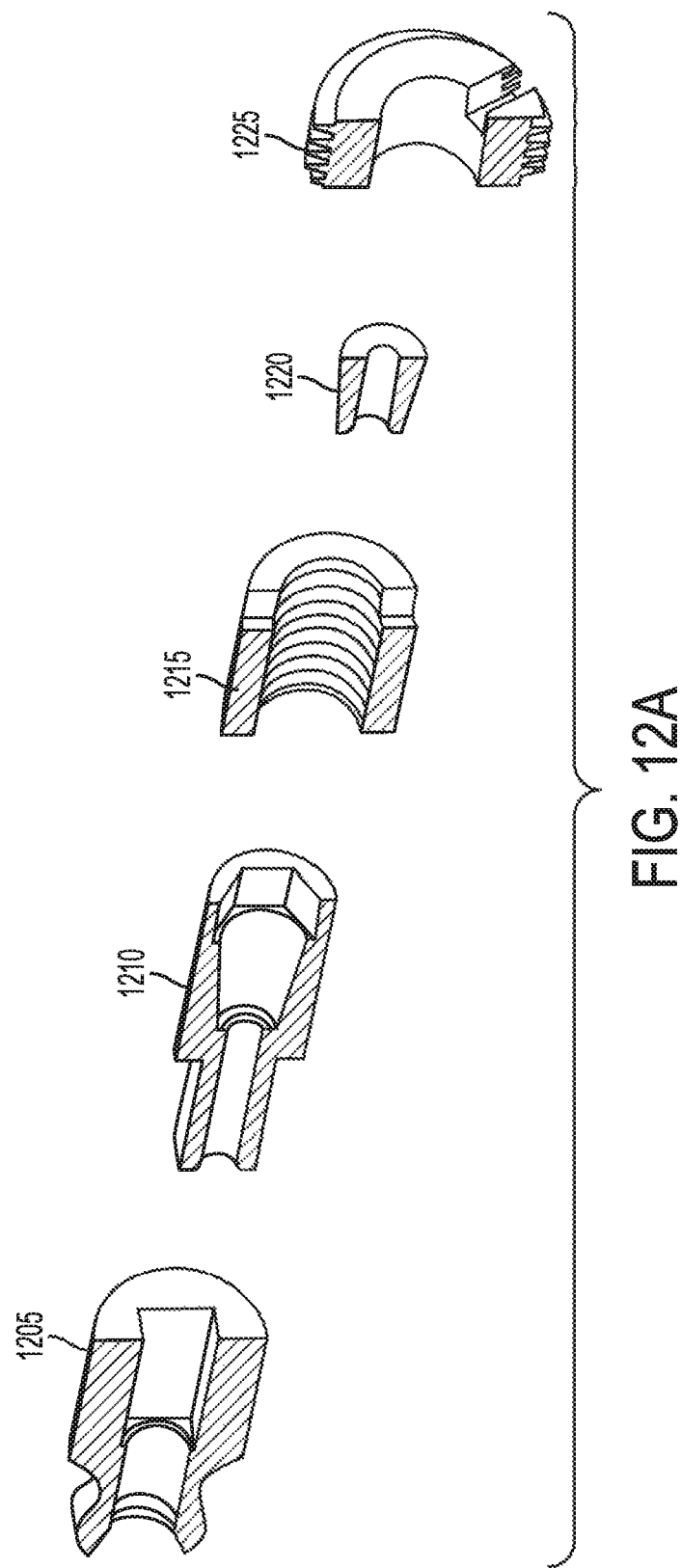
FIGS. 12A and 12B depict an exploded view and a cut-away view of an exemplary tensioning assembly according to an embodiment.
Figure 12B:
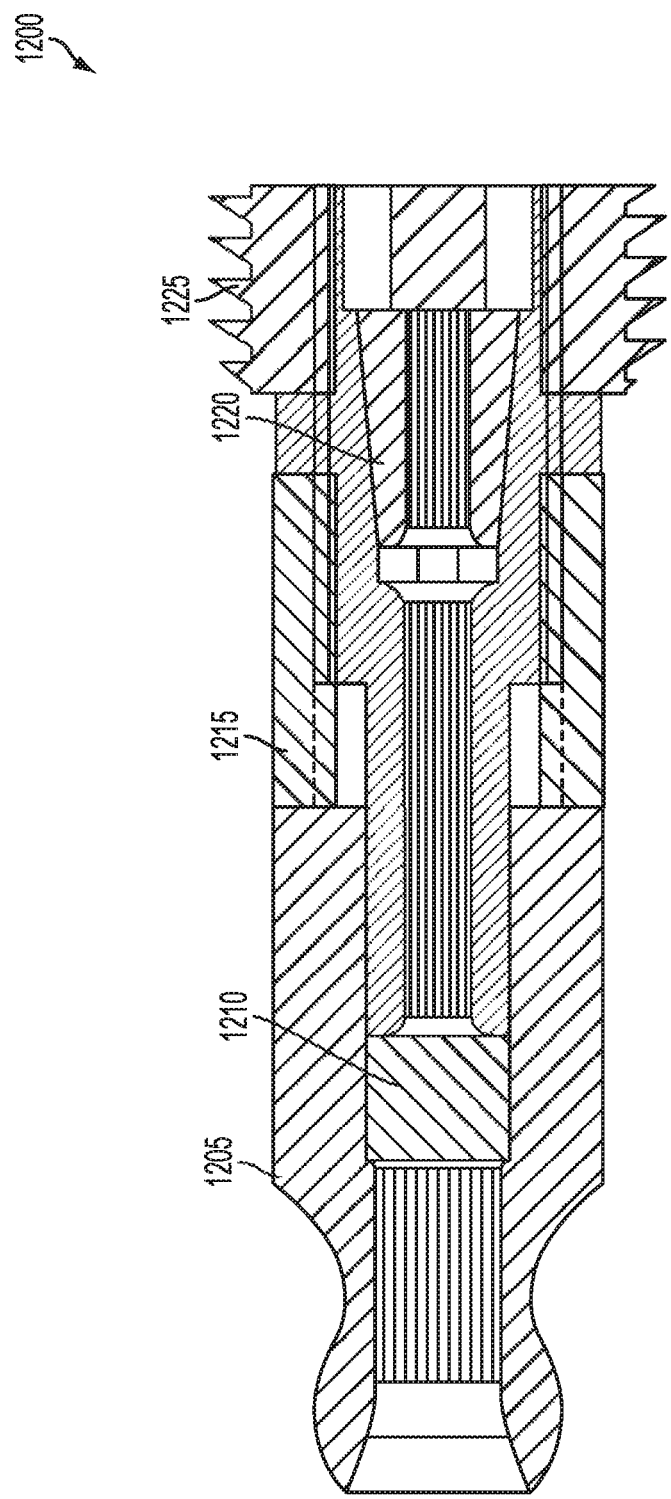

FIGS. 12A and 12B depict an exploded view and a cut-away view of an exemplary tensioning assembly 1115 according to an embodiment. As shown in FIG. 12A, the tensioning assembly 1115 may include a hex ball tensioner 1205, a cable anchor 1210, a tensioning sleeve 1215, a collet 1220 and a lock nut 1225. A stiffening cable may be located in the center of the tensioning assembly 1115, but is not shown in FIGS. 12A and 12B to enable better viewing of the remaining components of the tensioning assembly.

In an embodiment, the stiffening cable may be secured with the tapered collet 1220 resting in the socket of the cable anchor 1210. The tensioning sleeve 1215 may be threaded over the cable anchor 1210. The cable anchor 1210 may have a square rod which slides in the hex ball tensioner 1205. In operation, the cable anchor 1210 may be held in place by a user operated tool while the tensioning sleeve 1215 is threaded in. Threading in the tensioning sleeve 1215 may cause the cable anchor 1210 to be pushed out. A spline of the cable anchor 1210, when held by a user such as a surgeon, may prevent the entire assembly from rotating while the tensioning sleeve 1215 is rotated by a second external tool. The lock nut 1225 may be applied. In an embodiment, the lock nut 1225 may have the same thread pitch inside and out. As such, the lock nut 1225 may be threaded into the bone as it threads onto the cable anchor 1210 without drawing the cable anchor out of the bone, such as the pelvis, into which it is inserted. Application of the tensioning assembly 1115 may cause the flexible device to become rigid within the patient in order to assist in fixing the bone.

EXAMPLE 1: Kit for Medical Use

A kit may be sold to physicians, surgeons or other medical professionals or medical institutions for use in treating a bone fracture. The kit includes a flexible device similar to those discussed above (e.g., device 200 or device 800). The kit may also include a hammer drill (or hammer drill attachment for a surgical drill) and a guide wire configured to be attached to the hammer drill (or hammer drill attachment). The guide wire includes a bent section having a sharpened tip at a distal portion of the guide wire. An exemplary guide wire is disclosed in FIG. 13. The kit may also include a cannulated reamer. The cannulated reamer includes a flexible drive shaft and a bore configured to receive the guide wire. The kit may further include instructions for using the flexible device to treat a bone fracture. In particular, the kit may include instructions for using the hammer drill, guide wire and/or cannulated reamer to insert the guide wire into a bone and to use the cannulated reamer to form a tunnel in the bone using the guide wire as a guide. The instructions for inserting the guide wire using the hammer drill may include instructions for rotating the guide wire into a particular orientation based on the direction of the hole to be formed and instructions for using the hammer drill to form the hole.

EXAMPLE 2: Medical Device Using Expansion Sleeves

A flexible device for treating a bone includes a nitinol flexible tube having a plurality of slits configured to allow the flexible device to flex, a plurality of expansion sleeves contained within the flexible tube, and a cannula configured to actuate the bead segments. The cannula, when actuated, may cause each expansion sleeve to expand and abut an inner surface of the flexible tube, thereby causing the flexible device to become rigid. An exemplary medical device using expansion sleeves is disclosed in FIG. 2.

EXAMPLE 3: Expansion Sleeve with Silicone Cladding

An expansion sleeve includes a jam nut having expansion beads, silicone cladding covering at least a portion of the expansion beads, a plurality of expanding segments and a bore configured to receive a cannula. Adjacent expansion beads are configured to engage each other based on the size and shape of their adjacent surfaces when actuated. For example, adjacent surfaces may be convex and concave. Each of the expansion beads may taper down in diameter from an exposed surface to an internal surface of the bead. The jam nut is actuated by causing the expansion beads to be moved towards each other, which, in turn, causes the cladding to expand. As such, the expanding segments are configured to be in a non-actuated state against the cladding when the jam nut is not actuated. In contrast, when the jam nut is actuated, the cladding forces the expanding segments to abut an interior surface of the flexible tube. As such, the expanding segments cause the flexible tube to become rigid when the jam nut is in an actuated state.

EXAMPLE 4: Expansion Sleeve with Retaining Spring

An expansion sleeve includes expansion beads, a retaining spring, a plurality of expanding segments and a bore configured to receive a cannula. Adjacent expansion beads are configured to engage each other based on the size and shape of their adjacent surfaces when actuated. For example, adjacent surfaces may be convex and concave. The expansion sleeve is actuated by causing the expansion beads to be moved towards each other causing the expanding segments to be pushed towards an inner surface of the flexible tube. As such, the retaining spring is configured to restrain the expanding segments when in a nonactuated state. In contrast, when the actuator is actuated, the expanding segments are configured to abut an interior surface of the flexible tube. In this way, the expanding segments cause the flexible tube to become rigid when in an actuated state.

EXAMPLE 5: Expansion Sleeve with O-Rings

An expansion sleeve includes expansion beads, one or more O-rings, a plurality of expanding segments, and a bore configured to receive a cannula. Adjacent expansion beads are configured to engage each other based on the size and shape of their adjacent surfaces when actuated. For example, adjacent surfaces may be convex and concave. The expansion sleeve is actuated by causing the expansion beads to be moved towards each other causing the expanding segments to be pushed towards an inner surface of the flexible tube. As such, the one or more O-rings are configured to restrain the expanding segments when in a non-actuated state. In contrast, when the actuator is actuated, the expanding segments are configured to abut an interior surface of the flexible tube. As such, the expanding segments cause the flexible tube to become rigid when in an actuated state.

EXAMPLE 6: Medical Device Using Bead Segments

A flexible device for treating a bone includes a stainless steel flexible tube having a plurality of slits configured to allow the flexible device to flex, a plurality of bead segments contained within the flexible tube, and a cannula configured to actuate the bead segments. The cannula, when actuated, may cause each bead segment to engage adjacent bead segments, thereby stiffening the bead segments and causing the flexible device to become rigid. An exemplary medical device using bead segments is disclosed in FIG. 6.

EXAMPLE 7: Medical Device Using Rods

A flexible device includes a flexible tube, a sleeve within the flexible tube and a plurality of rods contained within the sleeve. The rods are configured to be connected to a distal end of the flexible tube and to bend as the flexible tube is flexed. The sleeve, when actuated, is configured to compress the rods together to restrict their movement in a lateral direction (i.e., in the proximal or distal directions with respect to the flexible tube). An exemplary medical device using rods is disclosed in FIG. 8.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Example Embodiments

Example 1 includes a device, comprising: segments forming a flexible body having first and second body ends and being configurable in a curved shape; at least one axial opening formed in the segments; flexible members disposed in at least one of the at least one axial opening, each flexible member configured to move relative to at least one of the segments along an axial direction as the flexible body is being manipulated into a curved shape; and a mechanism disposed at one of the first and second body ends and being configurable to prohibit the flexible members from moving relative to one another to lock the flexible body in a curved shape.

Example 2 includes the device of Example 1 wherein at least one of the segments includes a segment end that is engaged with a segment end of another one of the segments.

Example 3 includes the device of any of Examples 1-2 wherein at least one of the segments includes first and second segment ends having approximately a same shape.

Example 4 includes the device of any of Examples 1-3 wherein at least one of the segments includes a segment end having a portion that is disposed within a portion of a segment end of another one of the segments.

Example 5 includes the device of any of Examples 1-4 wherein at least one of the at least one axial opening extends through a respective center of each of the segments.

Example 6 includes the device of any of Examples 1-5 wherein the flexible members comprise respective rods.

Example 7 includes the device of any of Examples 1-6 wherein at least one of the flexible members is configured to move relative to at least another of the flexible members along the axial direction as the flexible body is being manipulated into a curved shape.

Example 8 includes the device of any of Examples 1-7 wherein the mechanism is configurable to prohibit the flexible members from moving along the axial direction relative to the segments to lock the flexible body into a curved shape.

Example 9 includes the device of any of Examples 1-8, further comprising a screw disposed at another of the first and second body ends and configured to secure the flexible body to a bone.

Example 10 includes the device of any of Examples 1-9 wherein the mechanism is configurable to lock the flexible body in a curved shape while at least a portion of the flexible body is disposed inside of a bone.

Example 11 includes the device of any of Examples 1-10 wherein the mechanism is configurable to lock the flexible body in a curved shape without changing the curved shape.

Example 12 includes the device of any of Examples 1-11 wherein the flexible members span a length of the flexible body.

Example 13 includes the device of any of Examples 1-12 wherein the mechanism is configured to transition from one of prohibiting the flexible members from moving relative to one another and allowing the flexible members to move relative to one another to the other of prohibiting the flexible members from moving and allowing the flexible members to move without changing a shape of the flexible body.

Example 14 includes the device of any of Examples 1-13 wherein at least one of the flexible members is configured to support, at least partially, a load imposed upon one or more of the segments while the flexible body is locked in a curved shape.

Example 15 includes a method, comprising: manipulating a flexible body into a curved shape, the flexible body including segments and at least one axial opening through the segments from one end of the flexible body to another end of the flexible body; and locking the flexible body in the curved shape by prohibiting flexible members that are disposed within at least one of the at least one axial opening from moving relative to one another.

Example 16 includes the method of Example 15 wherein manipulating the flexible body includes moving at least one of the flexible members along at least one of the at least one axial opening relative to at least one of the segments.

Example 17 includes the method of any of Examples 15-16 wherein manipulating the flexible body includes moving at least one of the flexible members along at least one of the at least one axial opening relative to at least one other of the flexible members.

Example 18 includes the method of any of Examples 15-17 wherein locking the flexible body in the curved shape further comprises prohibiting the flexible members from moving relative to the segments.

Example 19 includes the method of any of Examples 15-18 wherein manipulating the flexible body into a curved shape includes moving at least one of the segments relative to an adjacent one of the segments while the at least one of the segments and the adjacent one of the segments are in contact with one another.

Example 20 includes the method of any of Examples 15-19 wherein locking the flexible body in the curved shape includes locking the flexible body without changing the curved shape.

Although specific embodiments have been illustrated and described herein, it will be appreciated by those of ordinary skill in the art that any arrangement, which is calculated to achieve the same purpose, may be substituted for the specific embodiments shown. Therefore, it is manifestly intended that this invention be limited only by the claims and the equivalents thereof.

What is claimed is:

1. An apparatus for fixating a bone fracture, the apparatus comprising:
   a body configurable in a curve, the body having a proximal and a distal end portion;
   members disposed within the body, each of the members having a proximal end portion and a distal end portion, wherein the distal end portions of the members are fixed at an attachment location at the distal end portion of the body, and wherein the members are configured to move axially relative to one another without crossing over one another as the body is flexed into the curve such that a first one of the members traverses a distance between the attachment location and a locking location and a second one of the members traverses a different distance between the attachment and locking locations;
   a screw attached to the distal end portion of the body to enable the body to be inserted into a bone; and
   a mechanism configurable to apply a locking force normal to the members at the locking location to render the members incapable of relative axial movement such that the body retains the curve.

2. The apparatus of claim 1 wherein the body includes a flexible tube.

3. The apparatus of claim 1 wherein each of the members includes a respective flexible rod.

4. The apparatus of claim 1 wherein:
   the body includes at least one passageway; and
   the members are disposed within the at least one passageway.

5. The apparatus of claim 1 wherein the mechanism is configured to render the members incapable of relative axial movement by prohibiting each one of the members from moving axially relative to the others of the members.

6. The apparatus of claim 1 wherein,
   the mechanism is disposed adjacent to the proximal end portion of the body.

7. The apparatus of claim 1,
   wherein the mechanism includes, at the proximal end portion of the body, a lock that includes the locking location.

8. The apparatus of claim 1 wherein
   the locking location is adjacent to the proximal end portion of the body.

9. The apparatus of claim 1 wherein
   the mechanism is at the proximal end portion of the body.

10. An implantable intramedullary apparatus for fixating a bone fracture, the apparatus comprising:
    a body configurable in a curve, the body having a proximal end portion and a distal end portion;
    members disposed within the body, each of the member having a proximal end portion and a distal end portion, wherein the distal end portions of the members are fixed at an attachment location at the distal end portion of the body, and wherein a respective length of each member between the attachment location and a locking location is changeable as the body is flexed into the curve such that the length of a first one of the members between the attachment and locking locations is different than the length of a second one of the members between the attachment and locking locations, the members not crossing over one another while moving axially;
    a screw attached to the distal end portion of the body to enable the body to be inserted into a bone; and
    a mechanism configurable to apply a locking force normal to the members at the locking location to fix the body in the curve by prohibiting relative axial movement of the members.

11. The apparatus of claim 10 wherein
    the locking location is closer to the proximal end portion of the body than to the distal end portion of the body.

* * * * *

UNITED STATES PATENT AND TRADEMARK OFFICE
CERTIFICATE OF CORRECTION

| | |
|---|---|
| PATENT NO. | : 11,529,148 B2 |
| APPLICATION NO. | : 15/952093 |
| DATED | : December 20, 2022 |
| INVENTOR(S) | : Meek et al. |

It is certified that error appears in the above-identified patent and that said Letters Patent is hereby corrected as shown below:

In the Claims

In Column 17, in Claim 1, Lines 4-5, delete "proximal" and insert -- proximal end portion --, therefor.

In Column 17, in Claim 6, Line 35, delete "wherein," and insert -- wherein --, therefor.

Signed and Sealed this
Thirty-first Day of January, 2023

*Katherine Kelly Vidal*

Katherine Kelly Vidal
*Director of the United States Patent and Trademark Office*